(12) United States Patent
Fisher et al.

(10) Patent No.: US 9,776,964 B2
(45) Date of Patent: *Oct. 3, 2017

(54) PHENOXYETHYL CYCLIC AMINE DERIVATIVES AND THEIR ACTIVITY AS EP4 RECEPTOR MODULATORS

(71) Applicant: Eli Lilly and Company, Indianapolis, IN (US)

(72) Inventors: Matthew Joseph Fisher, Mooresville, IN (US); Steven Lee Kuklish, Fishers, IN (US); Peter Rudolph Manninen, Brownsburg, IN (US); Matthew Allen Schiffler, Indianapolis, IN (US); Alan M Warshawsky, Carmel, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/030,888

(22) PCT Filed: Dec. 11, 2014

(86) PCT No.: PCT/US2014/069743
§ 371 (c)(1),
(2) Date: Apr. 21, 2016

(87) PCT Pub. No.: WO2015/094902
PCT Pub. Date: Jun. 25, 2015

(65) Prior Publication Data
US 2016/0272585 A1    Sep. 22, 2016

Related U.S. Application Data

(60) Provisional application No. 61/916,827, filed on Dec. 17, 2013.

(51) Int. Cl.
C07D 211/44 (2006.01)
C07D 211/60 (2006.01)
C07D 217/26 (2006.01)
C07D 221/04 (2006.01)
C07D 221/20 (2006.01)
C07D 207/16 (2006.01)
C07D 209/52 (2006.01)
C07D 207/04 (2006.01)
C07D 211/06 (2006.01)

(52) U.S. Cl.
CPC .......... C07D 211/60 (2013.01); C07D 207/04 (2013.01); C07D 207/16 (2013.01); C07D 209/52 (2013.01); C07D 211/06 (2013.01); C07D 217/26 (2013.01); C07D 221/04 (2013.01); C07D 221/20 (2013.01)

(58) Field of Classification Search
CPC ............................ C07D 211/44; C07D 211/60
USPC .................... 546/221, 225; 514/327, 330
See application file for complete search history.

(56) References Cited

U.S. PATENT DOCUMENTS

| 7,414,071 | B2 | 8/2008 | Cameron et al. |
| 8,598,355 | B2 | 12/2013 | Nozawa et al. |
| 8,962,659 | B2 | 2/2015 | Schiffler et al. |
| 9,000,043 | B2 | 4/2015 | Manninen et al. |
| 9,402,838 | B2 * | 8/2016 | Schiffler ............ C07D 211/60 |
| 2005/0250818 | A1 | 11/2005 | Koike et al. |
| 2011/0136887 | A1 | 6/2011 | Yuan |
| 2015/0126555 | A1 | 5/2015 | Schiffler et al. |

FOREIGN PATENT DOCUMENTS

| GB | 1538482 | 1/1979 |
| WO | WO2005021508 | 3/2005 |
| WO | WO2005105732 | 11/2005 |
| WO | WO2005105733 | 11/2005 |
| WO | WO2007121578 | 11/2007 |
| WO | WO2007143825 | 12/2007 |
| WO | WO2011102149 | 8/2011 |
| WO | WO2013004290 | 1/2013 |
| WO | WO2013004291 | 1/2013 |

OTHER PUBLICATIONS

Borriello, M., et al, Preparation of cyclic amine derivatives as EP4 receptor agonists for therapy of prostaglandin E mediated diseases CA158:158421 (2013).

* cited by examiner

Primary Examiner — Patricia L Morris
(74) Attorney, Agent, or Firm — Nelsen L. Lentz

(57) ABSTRACT

The present invention provides a compound of the Formula (I): wherein X, R, $R^1$, $R^2$, $R^3$, $R^4$, $R^5$, $R^6$, $R^7$, $R^8$, and $R^9$ are as defined herein, or a pharmaceutically acceptable salt thereof.

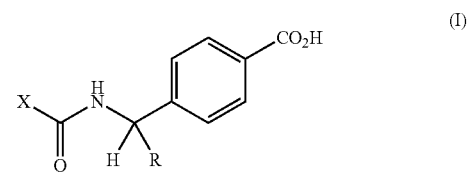

7 Claims, No Drawings

PHENOXYETHYL CYCLIC AMINE DERIVATIVES AND THEIR ACTIVITY AS EP4 RECEPTOR MODULATORS

The present invention relates to certain novel phenoxyethyl compounds, to pharmaceutical compositions comprising the compounds, to methods of using the compounds to treat physiological disorders, and to intermediates and processes useful in the synthesis of the compounds.

The present invention is in the field of treatment of inflammatory conditions, such as arthritis, including osteoarthritis and rheumatoid arthritis, and further including pain associated with these conditions. Arthritis affects millions of patients in the United States alone and is a leading cause of disability. Treatments often include NSAIDs (non-steroidal anti-inflammatory drugs) or COX-2 inhibitors, which may produce untoward cardiovascular side effects. As such, patients who have a poor cardiovascular profile, such as hypertension, may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3 and EP4. It has been disclosed that EP4 is the primary receptor involved in joint inflammatory pain in rodent models of rheumatoid arthritis and osteoarthritis (See *J. Pharmacol. Exp. Ther.,* 325, 425 (2008)). Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors. (See for example *Bioorganic & Medicinal Chemistry Letters,* 21, 484 (2011)).

WO 2013/004290 discloses certain cyclic amine derivatives having EP4 receptor antagonist activity. WO 2013/004291 discloses certain cyclic amine derivatives having EP4 receptor agonist activity.

The present invention provides certain novel compounds that are inhibitors of EP4 and certain novel compounds that are selective inhibitors of EP4 relative to EP1, EP2, and EP3. In addition, the present invention provides certain novel compounds with the potential for reduced cardiovascular or gastrointestinal side effects in comparison to traditional NSAIDs.

Accordingly, the present invention provides a compound of the Formula I:

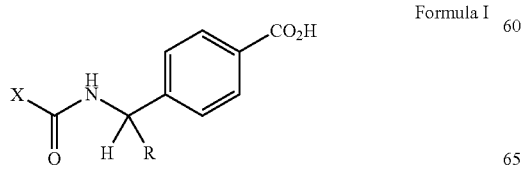

Formula I wherein X is:

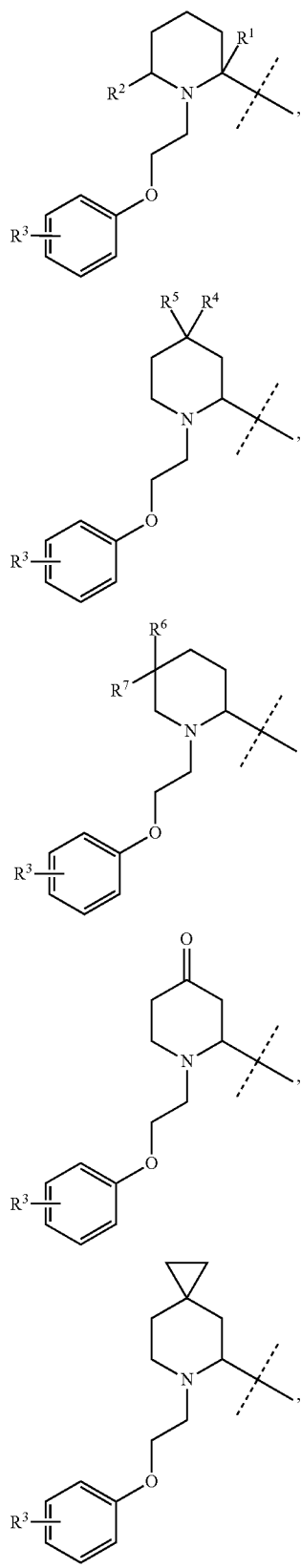

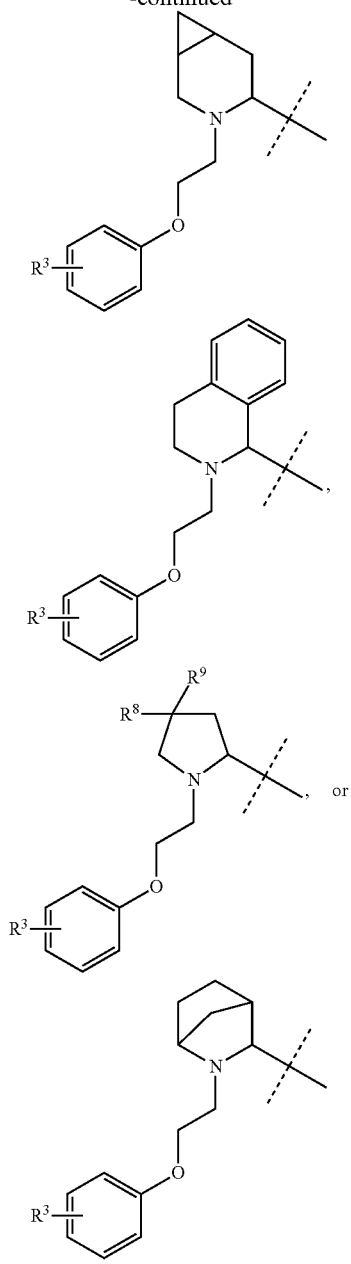

R is H, methyl, or ethyl;
R$^1$ is methyl, when R$^2$ is H, and R$^1$ is H when R$^2$ is methyl;
R$^3$ is H or F;
R$^4$ is H, F, or methyl;
R$^5$ is OH, methyl, methoxy, or F;
R$^6$ is H when R$^7$ is OH, and R$^6$ is F when R$^7$ is F; and
R$^8$ and R$^9$ are each independently H or F;
or a pharmaceutically acceptable salt thereof.

The present invention also provides a method of treating arthritis in a patient, comprising administering to a patient in need of such treatment an effective amount of a compound of Formula I, or a pharmaceutically acceptable salt thereof. The present invention also provides a method of treating osteoarthritis in a patient, comprising administering to a patient in need of such treatment an effective amount of a compound of Formula I, or a pharmaceutically acceptable salt thereof. In addition, the present invention provides a method of treating rheumatoid arthritis in a patient, comprising administering to a patient in need of such treatment an effective amount of a compound of Formula I, or a pharmaceutically acceptable salt thereof. The present invention also provides a method of treating pain associated with arthritis in a patient, comprising administering to a patient in need of such treatment an effective amount of a compound of Formula I, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I, or a pharmaceutically acceptable salt thereof.

Furthermore, the invention provides a compound of Formula I, or a pharmaceutically acceptable salt thereof for use in therapy. In addition, the invention provides a compound of Formula I, or a pharmaceutically acceptable salt thereof for use in the treatment of arthritis. Furthermore, the invention provides a compound of Formula I, or a pharmaceutically acceptable salt thereof for use in the treatment of osteoarthritis. In addition, the invention provides a compound of Formula I, or a pharmaceutically acceptable salt thereof for use in the treatment of rheumatoid arthritis. The invention also provides a compound of Formula I, or a pharmaceutically acceptable salt thereof for use in the treatment of pain associated with osteoarthritis or rheumatoid arthritis. The invention also provides the use of a compound of Formula I, or a pharmaceutically acceptable salt thereof, for the manufacture of a medicament for the treatment of arthritis. Furthermore, the invention provides the use of a compound of Formula I, or a pharmaceutically acceptable salt thereof, for the manufacture of a medicament for the treatment of osteoarthritis. The invention provides the use of a compound of Formula I, or a pharmaceutically acceptable salt thereof, for the manufacture of a medicament for the treatment of rheumatoid arthritis. The present invention also provides the use of a compound of Formula I, or a pharmaceutically acceptable salt thereof, for the manufacture of a medicament for the treatment of pain associated with osteoarthritis or rheumatoid arthritis.

The invention further provides a pharmaceutical composition comprising a compound of Formula I, or a pharmaceutically acceptable salt thereof, with one or more pharmaceutically acceptable carriers, diluents, or excipients. In a particular embodiment, the composition further comprises one or more other therapeutic agents. This invention also encompasses novel intermediates and processes for the synthesis of the compound of Formula I, or a pharmaceutically acceptable salt thereof.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I, or pharmaceutically acceptable salt thereof, are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

It is preferred that R is methyl.
It is most preferred that when R is methyl, $R^3$ is H.
It is preferred that when $R^4$ is F, $R^5$ is F.
It is further preferred that when $R^4$ is methyl, $R^5$ is methyl.
It is preferred that when $R^8$ is F, $R^9$ is F.
It is preferred that X is:

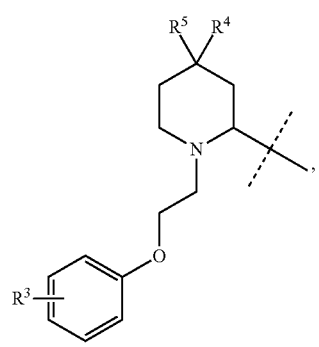

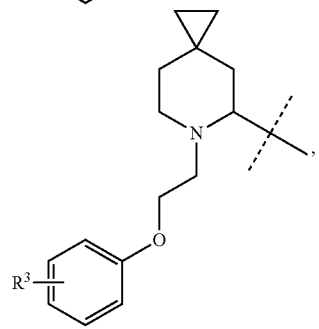

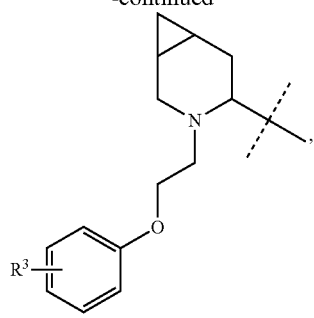

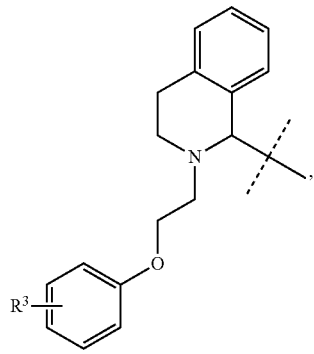

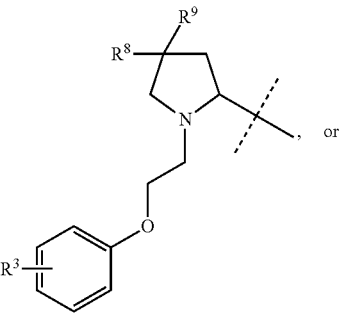, or

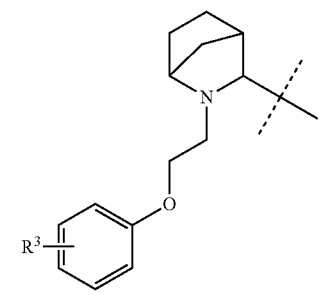

It is most preferred that X is:

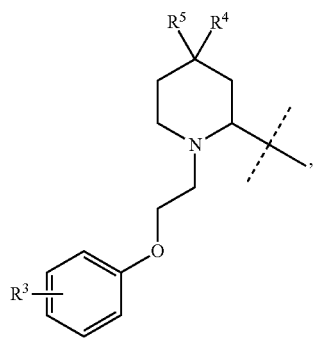

-continued
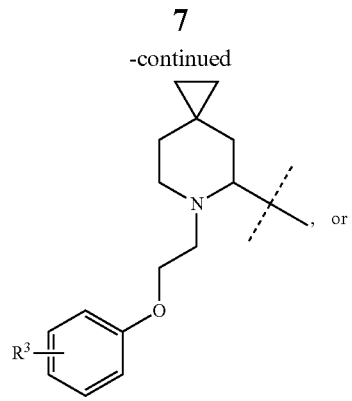, or
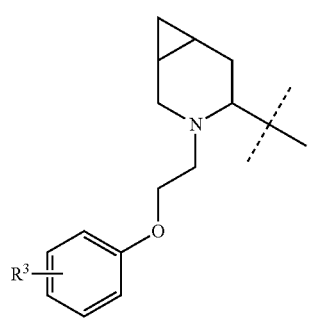
It is most preferred that when R is methyl, R³ is H and X is:
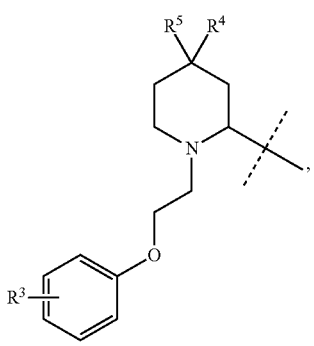
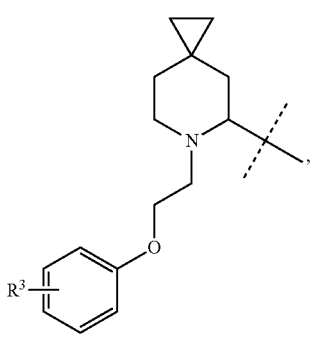
-continued
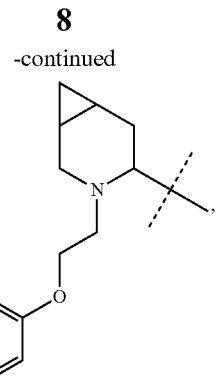
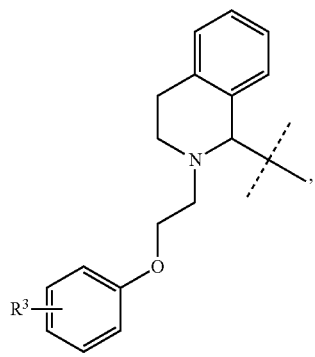
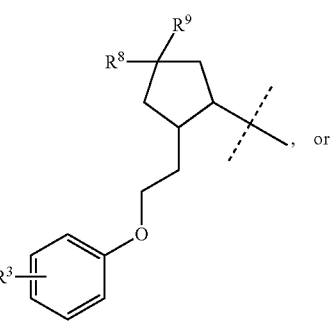, or
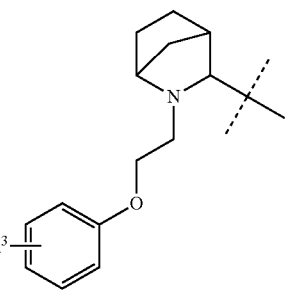
It is most especially preferred that when R is methyl, R³ is H and X is:
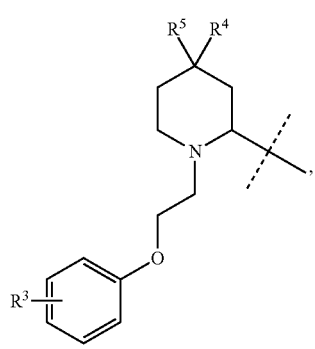

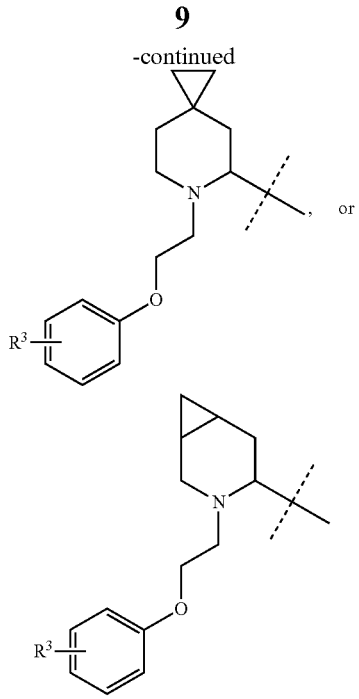, or

Preferred compounds are:
4-((1S)-1-(((1S,3R,4R)-2-(2-phenoxyethyl)-2-azabicyclo[2.2.1]heptan-3-carbonyl)amino)ethyl)benzoic acid;
4-((1S)-1-(((5R)-6-(2-(4-fluorophenoxy)ethyl)-6-azaspiro[2.5]octane-5-carbonyl)amino)ethyl)benzoic acid;
4-((1S)-1-(((5R)-6-(2-phenoxyethyl)-6-azaspiro[2.5]octane-5-carbonyl)amino)ethyl)benzoic acid;
4-((1S)-1-(((1S,4R,6S)-3-(2-phenoxyethyl)-3-azabicyclo[4.1.0]heptane-4-carbonyl)amino)ethyl)benzoic acid;
4-((1S)-1-(((2R)-1-(2-phenoxyethyl)-4,4-difluoropiperidin-2-carbonyl)amino)ethyl)benzoic acid;
4-((1S)-1-(((2S)-1-(2-phenoxyethyl)-4,4-difluoropiperidin-2-carbonyl)amino)ethyl)benzoic acid;
4-((1 S)-1-(((2R*)-1-(2-phenoxyethyl)-4,4-dimethylpiperidin-2-carbonyl)amino)ethyl)benzoic acid;
4-((1S)-1-(((2R)-1-(2-(4-fluorophenoxy)ethyl)4,4-difluoropyrrolidin-2-carbonyl)amino)ethyl)benzoic acid;
4-((1S)-1-(((1R)-2-(2-phenoxyethyl)-1,2,3,4-tetrahydroisoquinolin-1-carbonyl)amino)ethyl)benzoic acid;
and the pharmaceutically acceptable salts thereof.
Especially preferred compounds are:
4-((1S)-1-(((5R)-6-(2-(4-fluorophenoxy)ethyl)-6-azaspiro[2.5]octane-5-carbonyl)amino)ethyl)benzoic acid;
4-((1S)-1-(((5R)-6-(2-phenoxyethyl)-6-azaspiro[2.5]octane-5-carbonyl)amino)ethyl)benzoic acid;
4-((1S)-1-(((1S,4R,6S)-3-(2-phenoxyethyl)-3-azabicyclo[4.1.0]heptane-4-carbonyl)amino)ethyl)benzoic acid;
4-((1S)-1-(((2R)-1-(2-phenoxyethyl)-4,4-difluoropiperidin-2-carbonyl)amino)ethyl)benzoic acid;
and the pharmaceutically acceptable salts thereof.

As used herein, "h" refers to hours; "kPag" refers to kilopascals gauge pressure; "Boc" refers to a tert-butoxycarbonyl protecting group; "DMEM" refers to Dulbecco's Modified Eagle's Medium; "ACN" refers to acetonitrile; "DIEA" refers to N,N-diisopropylethylamine; "DMAP" refers to 4-(N,N-dimethylamino)pyridine; "DMSO" refers to dimethylsulfoxide; "DMF" refers to N,N-dimethylformamide; "EtOH" refers to ethanol; "THF" refers to tetrahydrofuran; "MeOH" refers to methanol; "EtOAc" refers to ethyl acetate; "Et$_2$O" refers to diethyl ether; "TBME" refers to tert-butyl methyl ether; "BOP" refers to benzotriazol-1-yloxytris(dimethylamino)phosphonium hexafluorophosphate; "Cbz" refers to a benzyloxy carbamate protecting group; "mCPBA" refers to 3-chloroperbenzoic acid; "KHMDS" refers to potassium bis(trimethylsilyl)amide; "PGE$_2$" refers to prostaglandin E$_2$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl]ethanesulfonic acid); "HTRF" refers to homogeneous time-resolved fluorescence technology; "HEK" refers to human embryonic kidney; "HBSS" refers to Hank's Balanced Salt Solution; "EC$_{80}$" refers to the concentration of an agent that produces 80% of the maximal efficacy possible for that agent; and "IC$_{50}$" refers to the concentration of an agent that produces 50% of the maximal inhibitory response possible for that agent. "Ph" refers to a phenyl group of the following structure:

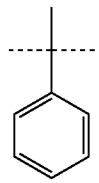

Pharmaceutically acceptable salts and common methodology for preparing them are well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One skilled in the art of synthesis will appreciate that the compounds of the present invention are readily converted to and may be isolated as a pharmaceutically acceptable salt, such as a hydrochloride salt, using techniques and conditions well known to one of ordinary skill in the art. In addition, one skilled in the art of synthesis will appreciate that the compounds of Formula I are readily converted to and may be isolated as the corresponding free base or free acid from the corresponding pharmaceutically acceptable salt.

The present invention contemplates all individual enantiomers or diastereomers, as well as mixtures of the enantiomers and diastereomers of said compounds including racemates. Individual isomers, enantiomers, or diastereomers may be separated or resolved by one of ordinary skill in the art at any convenient point in the synthesis of compounds of the present invention by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wien, "*Stereochemistry of Organic Compounds*", Wiley-Interscience, 1994).

The compound of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compound of Formula I, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

PREPARATION 1

Synthesis of ethyl (2R*,6R*)-6-methyl-1-(2-phenoxyethyl)piperidine-2-carboxylate (racemic)

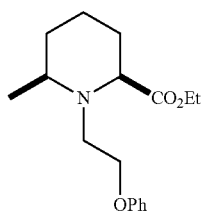 [SMILES: CCOC(=O)[C@@H]1CCC[C@H](C)N1CCOc1ccccc1]

Under a nitrogen atmosphere, heat a mixture of ethyl (2R*,6R*)-6-methylpiperidine-2-carboxylate hydrochloride (500 mg, 2.41 mmol), DMF (6.0 mL), potassium carbonate (998 mg, 7.22 mmol), and β-bromophenetole (494 mg, 2.41 mmol) to 100° C. with stirring overnight. Allow the reaction mixture to cool to room temperature, then dilute with EtOAc (100 mL). Wash the mixture with water (2×50 mL) and then saturated aqueous NaCl solution (2×50 mL), discarding the aqueous phase after each wash. Dry the organic phase over MgSO$_4$, remove the solids by filtration, and concentrate the filtrate under reduced pressure to furnish a yellow oil. Subject the crude material to flash chromatography on silica gel, eluting with a gradient of 0% to 60% EtOAc in hexanes, to furnish the title compound as a colorless oil (200 mg, 29% yield). Mass spectrum (m/z): 292 (M+H)$^+$.

PREPARATION 2

Synthesis of benzyl (R)-1-tert-butoxycarbonyl-4-oxopiperidine-2-carboxylate

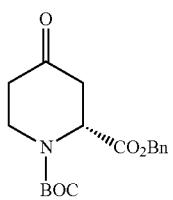 [SMILES: CC(C)(C)OC(=O)N1CCC(=O)C[C@@H]1C(=O)OCc1ccccc1]

To a solution of (R)-1-tert-butoxycarbonyl-4-oxopiperidine-2-carboxylic acid (7.00 g, 28.8 mmol) in CH$_2$Cl$_2$ (100 mL) at 0° C., add benzyl alcohol (2.98 mL, 28.8 mmol), dicyclohexylcarbodiimide (6.60 g, 31.7 mmol), and DMAP (352 mg, 2.88 mmol). Allow the mixture to warm to room temperature with stirring overnight. Filter the mixture to remove the solids, and concentrate the filtrate under reduced pressure to furnish a crude material. Subject this material to flash chromatography on silica gel, eluting with a gradient of 0% to 20% EtOAc in hexanes, to furnish the title compound as a colorless oil (6.10 g, 64% yield). Mass spectrum (m/z): 234 (M+2H-Boc), 356 (M+Na)$^+$.

Scheme 1

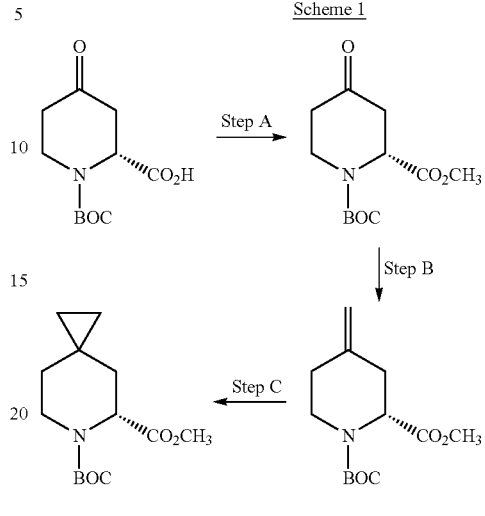

PREPARATION 3

Synthesis of methyl (R)-1-tert-butoxycarbonyl-4-oxopiperidine-2-carboxylate

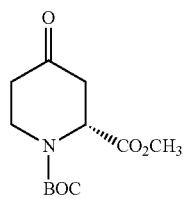

Scheme 1, Step A: To a room-temperature solution of (R)-1-tert-butoxycarbonyl-4-oxopiperidine-2-carboxylic acid (1.05 g, 4.32 mmol) in DMF (5.0 mL), add cesium carbonate (1.55 g, 4.75 mmol) and stir for 5 min. Then, add iodomethane (403 μL, 6.47 mmol) in a dropwise fashion over 15 min. Upon completion of the addition, stir the mixture at room temperature overnight. Then, add water (25 mL), and extract the aqueous mixture with TBME (2×75 mL). Dry the combined organic phases over Na$_2$SO$_4$, filter, and concentrate the filtrate under reduced pressure to furnish the title compound as a white solid (1.10 g, 99% yield). Mass spectrum (m/z): 280 (M+Na)$^+$.

PREPARATION 4

Synthesis of methyl (R)-1-tert-butoxycarbonyl-4-methylenepiperidine-2-carboxylate

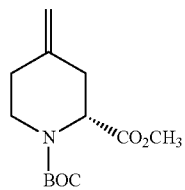 [SMILES: C=C1CCN(C(=O)OC(C)(C)C)[C@@H](C(=O)OC)C1]

Scheme 1, Step B: Under a nitrogen atmosphere, to a 0° C. mixture of methyltriphenylphosphonium bromide (3.90 g, 10.92 mmol) and anhydrous toluene (40 mL), add KHMDS (0.5 M solution in toluene, 19 mL, 9.5 mmol) in a dropwise fashion over 15 min. Then, allow the mixture to warm to room temperature, then stir for two hours. Cool the mixture to 0° C., and add a solution of methyl (R)-1-tert-butoxycarbonyl-4-oxopiperidine-2-carboxylate (1.10 g, 4.28 mmol) in toluene (40 mL) in a dropwise fashion over 15 min Allow the mixture to warm to room temperature, then stir for six hours and then hold the mixture at room temperature for three days. Add a saturated aqueous solution of NH$_4$Cl (100 mL), and extract the mixture with CH$_2$Cl$_2$ (2×250 mL). Dry the combined organic layers over Na$_2$SO$_4$, filter, and concentrate the filtrate under reduced pressure. Subject the resulting crude material to flash chromatography on silica gel, eluting with a gradient of 0% to 40% EtOAc in hexanes, to furnish the title compound (920 mg, 84% yield). Mass spectrum (m/z): 278 (M+Na)$^+$, 533 (2M+Na)$^+$.

Prepare the following compound essentially by the method of Preparation 4, using the appropriate ketone in place of methyl (R)-1-tert-butoxycarbonyl-4-oxopiperidine-2-carboxylate:

| No. | Chemical Name | Structure | MS (m/z) |
|---|---|---|---|
| 5 | benzyl (R)-1-tert-butoxycarbonyl-4-methylenepiperidine-2-carboxylate | 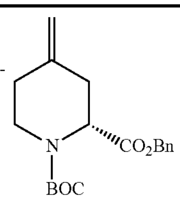 | 232 (M + 2H − Boc)$^+$, 354 (M + Na)$^+$ |

PREPARATION 6

Synthesis of methyl (R)-6-tert-butoxycarbonyl-6-azaspiro[2.5]octane-5-carboxylate

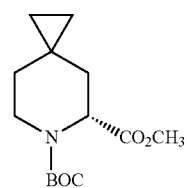 [SMILES: COC(=O)[C@H]1CC2(CCN1C(=O)OC(C)(C)C)CC2]

Scheme 1, Step C: To a 0° C. solution of methyl (R)-1-tert-butoxycarbonyl-4-methylenepiperidine-2-carboxylate (920 mg, 3.60 mmol) in Et$_2$O (25 mL) under a nitrogen atmosphere, add diazomethane (0.72 M solution in Et$_2$O, 25 mL, 18.0 mmol) in a dropwise fashion over 45 minutes. During the diazomethane addition, add seven portions of Pd(OAc)$_2$ (25 mg, 0.11 mmol; total 175 mg, 0.77 mmol) at six-minute intervals. Allow the mixture to warm to room temperature with stirring overnight. Add acetic acid (100 μL, 1.75 mmol), then remove the solids by filtration, rinsing through with CH$_2$Cl$_2$ (10 mL). Concentrate the combined filtrates under reduced pressure to furnish a mixture containing the title compound (1.08 g, 111% nominal yield). Mass spectrum (m/z): 292 (M+Na)$^+$.

Prepare the following compound essentially by the method of Preparation 6, using the appropriate alkene in place of methyl (R)-1-tert-butoxycarbonyl-4-methylenepiperidine-2-carboxylate:

| No. | Chemical Name | Structure | MS (m/z) |
|---|---|---|---|
| 7 | benzyl (R)-6-tert-butoxycarbonyl-6-azaspiro[2.5]octane-5-carboxylate | 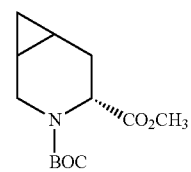 | 246 (M + 2H − Boc)$^+$ |

PREPARATION 8

Synthesis of methyl (1R*,4R,6R*)-3-tert-butoxycarbonyl-3-azabicyclo[4.1.0]heptane-4-carboxylate Batch 1. To a 0° C. solution of methyl (R)-1-tert-butoxycarbonyl-3,6-dihydro-2H-pyridine-2-carboxylate (800 mg, 3.32 mmol) in diethyl ether (50 mL), add diazomethane (0.72 M solution in Et$_2$O, 50 mL, 36.0 mmol) in 1.0-mL portions over 15 minutes. During the diazomethane addition, add four portions of Pd(OAc)$_2$ (12.5 mg, 0.055 mmol; total 50 mg, 0.22 mmol) at three-minute intervals. Stir the mixture for 35 min, then add acetic acid (1.0 mL, 17.5 mmol) and EtOAc (100 mL). Wash the combined mixture with saturated aqueous NaHCO$_3$ (100 mL) and saturated aqueous NaCl (100 mL). Dry the organic phase over Na$_2$SO$_4$, filter, and concentrate the filtrate under reduced pressure to furnish a crude brown oil (898 mg) as an 87:13 mixture of the title compound and unreacted starting alkene.

Batch 2. To a 0° C. solution of methyl (R)-1-tert-butoxycarbonyl-3,6-dihydro-2H-pyridine-2-carboxylate (800 mg, 3.32 mmol) in diethyl ether (50 mL), add diazomethane (0.72 M solution in Et$_2$O, 50 mL, 36.0 mmol) in 1.0-mL portions over 15 minutes. During the diazomethane addition, add four portions of Pd(OAc)$_2$ (12.5 mg, 0.055 mmol; total 50 mg, 0.22 mmol) at three-minute intervals. Stir the mixture for 35 min, then add acetic acid (1.0 mL, 17.5 mmol) and EtOAc (100 mL). Wash the combined mixture with saturated aqueous NaHCO$_3$ (100 mL) and saturated aqueous NaCl (100 mL). Dry the organic phase over Na$_2$SO$_4$, filter, and concentrate the filtrate under reduced pressure to furnish a crude brown oil (841 mg) as an 86:14 mixture of the title compound and unreacted starting alkene.

Dissolve the combined crude material of Batch 1 and 2 (1.74 g) in CH$_2$Cl$_2$ (18.7 mL) and cool to 0° C. Add mCPBA (647 mg, 1.87 mmol) and allow the mixture to warm to room temperature overnight with stirring. Add a second portion of mCPBA (323 mg, 0.88 mmol) and stir for an additional 5.5 hours at room temperature. Add saturated aqueous Na$_2$SO$_3$ (8 mL) and stir vigorously for 10 min. Dilute the mixture with EtOAc (150 mL), and wash with saturated aqueous NaHCO$_3$ (100 mL) and saturated aqueous NaCl (100 mL). Dry the organic phase over Na$_2$SO$_4$, filter, and concentrate the filtrate under reduced pressure. Subject the resulting crude material to flash chromatography on silica gel, eluting with a gradient of 0% to 100% CH$_2$Cl$_2$ in hexanes then with a gradient of 0% to 10% CH$_3$OH in CH$_2$Cl$_2$, to furnish the title compound as a mixture of two diastereomers (1.39 g, 85% yield). Mass spectrum (m/z): 156 (M+2H-Boc)$^+$.

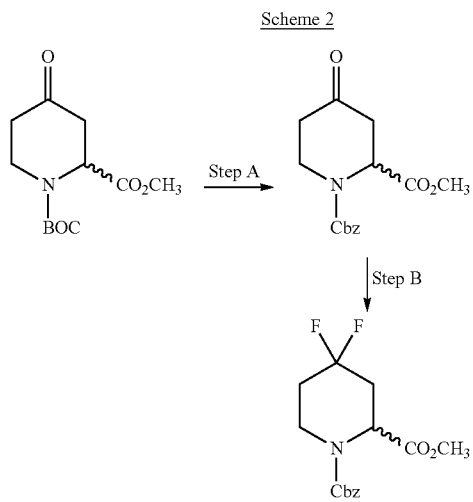

Scheme 2

PREPARATION 9

Synthesis of (±)-methyl 1-benzyloxycarbonyl-4-oxopiperidine-2-carboxylate (racemic)

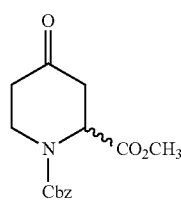 [SMILES: COC(=O)C1CC(=O)CCN1C(=O)OCc1ccccc1]

Scheme 2, Step A: Dissolve racemic (±)-methyl 1-tert-butoxycarbonyl-4-oxopiperidine-2-carboxylate (5.00 g, 19.4 mmol) in a solution of HCl in 1,4-dioxane (4.0 M, 48.6 mL, 194 mmol) and stir the mixture at room temperature overnight. Concentrate the mixture under reduced pressure and place in a 40° C. vacuum oven for 2 h to remove residual acid. Then, add CH$_2$Cl$_2$ (97 mL), benzyl chloroformate (3.65 g, 21.38 mmol), and DDEA (7.46 mL, 42.8 mmol), and stir at room temperature for 2 days. Add aqueous hydrochloric acid (1.0 N, 100 mL), and stir the mixture vigourously for 15 min Separate the organic layer, dry over MgSO$_4$, filter, and concentrate under reduced pressure to furnish a crude orange oil. Subject the crude material to flash chromatography on silica gel, eluting with a gradient of 50% to 100% EtOAc in hexanes, to furnish the title compound as a colorless, viscous oil (2.44 g, 43% yield). Mass spectrum (m/z): 292 (M+H)$^+$, 314 (M+Na)$^+$.

PREPARATION 10

Synthesis of (±)-methyl 1-benzyloxycarbonyl-4,4-difluoropiperidine-2-carboxylate (racemic)

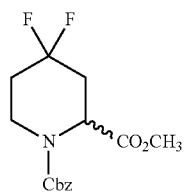

Scheme 2, Step B: Cool a solution of racemic (±)-methyl 1-benzyloxycarbonyl-4-oxopiperidine-2-carboxylate (2.44 g, 8.38 mmol) in THF (25 mL) to 0° C., then add diethylaminosulfur trifluoride (10.1 g, 62.8 mmol) dropwise at such a rate that the internal temperature remains below 5° C. Stir the mixture at 0° C. for 2 h, then at room temperature overnight. Cool the mixture to 0° C. and add water (50 mL) carefully in a dropwise fashion at such a rate that the internal temperature remains below 20° C. Add EtOAc (250 mL), water (50 mL), and saturated aqueous NaHCO$_3$ (200 mL), then separate the layers and wash the organic layer with saturated aqueous NaCl (200 mL), dry over MgSO$_4$, filter, and concentrate the filtrate under reduced pressure. Subject the resulting crude material to flash chromatography on silica gel, eluting with a gradient of 20% to 70% EtOAc in hexanes, to furnish the title compound as a colorless, viscous oil (1.24 g, 47%). Mass spectrum (m/z): 314 (M+H)$^+$, 331 (M+NH$_4$)$^+$, 336 (M+Na)$^+$.

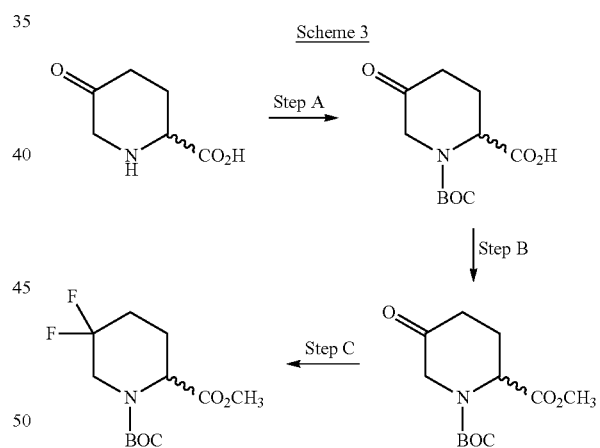

Scheme 3

PREPARATION 11

Synthesis of (±)-1-tert-butoxycarbonyl-5-oxopiperidine-2-carboxylic acid (racemic)

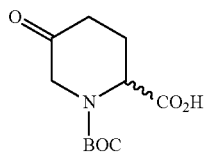 [SMILES: CC(C)(C)OC(=O)N1CC(=O)CCC1C(=O)O]

Scheme 3, Step A: To a stirring mixture of racemic (±)-5-oxopiperidine-2-carboxylic acid (1.00 g, 6.99 mmol) and CH$_2$Cl$_2$ (14.0 mL) at 0° C., add di-tert-butyldicarbonate (1.60 g, 7.68 mmol) and triethylamine (1.07 mL, 7.34 mmol), and allow the mixture to warm to room temperature with stirring overnight. Add an aqueous solution of HCl (1.0 N) until the pH reaches 3.0, then extract the mixture with EtOAc (3×25 mL). Wash the combined organic phases with saturated aqueous NaCl (50 mL), dry over MgSO$_4$, filter, and concentrate the filtrate under reduced pressure to furnish the title compound as a tan solid (1.30 g, 77% yield). Mass spectrum (m/z): 144 (M+2H-Boc)$^+$, 188 (M+2H-t-Bu)$^+$, 266 (M+Na)$^+$.

PREPARATION 12

Synthesis of (±)-methyl 1-tert-butoxycarbonyl-5-oxopiperidine-2-carboxylate (racemic)

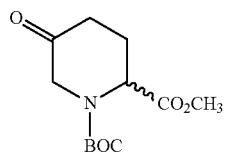 [SMILES: COC(=O)C1CCC(=O)CN1C(=O)OC(C)(C)C]

Scheme 3, Step B: To a stirring mixture of (±)-1-tert-butoxycarbonyl-5-oxopiperidine-2-carboxylic acid (1.30 g, 5.34 mmol) in toluene (8 mL) and CH$_3$OH (2 mL) at 0° C., add trimethylsilyldiazomethane (2.94 mL, 5.34 mmol) in dropwise fashion, then allow the mixture to warm to room temperature and stir for 1 h. Concentrate the mixture under reduced pressure to furnish the title compound as a light yellow oil (1.30 g, 95% yield). Mass spectrum (m/z): 158 (M+2H-Boc)$^+$, 202 (M+2H-t-Bu)$^+$.

PREPARATION 13

Synthesis of (±)-methyl 1-tert-butoxycarbonyl-5,5-difluoropiperidine-2-carboxylate (racemic)

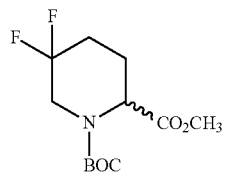

Scheme 3, Step C: To a stirring, room-temperature mixture of triethylamine trihydrofluoride (4.9 mL, 30.3 mmol), CH$_2$Cl$_2$ (42.9 mL), and triethylamine (1.76 mL, 12.6 mmol), add N,N-Diethylamino-S,S-difluorosulfinium tetrafluoroborate (5.21 g, 22.74 mmol), followed by a solution of (±)-methyl 1-tert-butoxycarbonyl-5-oxopiperidine-2-carboxylate (1.30 g, 5.05 mmol) in CH$_2$Cl$_2$ (2.53 mL), then stir the mixture at room temperature overnight. With vigourous stirring, carefully add a saturated aqueous solution of NaHCO$_3$ (100 mL) (Caution! Intense effervescence!), then extract the mixture with CH$_2$Cl$_2$ (2×100 mL). Dry the combined organic phases over Na$_2$SO$_4$, filter, and concentrate the filtrate under reduced pressure. Subject the resulting crude material to flash chromatography on silica gel, eluting with a gradient of 5% to 30% EtOAc in hexanes, to furnish the title compound as a colorless oil (610 mg, 43% yield). Mass spectrum (m/z): 302 (M+Na)$^+$.

PREPARATION 14

Synthesis of (2R*,5S*)-1-(2-phenoxyethyl)-5-hydroxypiperidine-2-carboxylic acid hydrochloride (racemic)

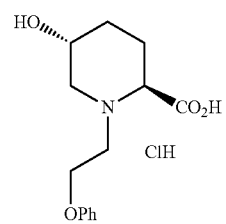 [SMILES: O=C(O)[C@@H]1CC[C@@H](O)CN1CCOc1ccccc1 ; Cl]

Stir a mixture of racemic (2R*,5S*)-5-hydroxypiperidine-2-carboxylic acid (150 mg, 1.03 mmol), 2-phenoxyacetaldehyde (281 mg, 2.07 mmol), acetic acid (59 µL, 1.03 mmol), and 1,2-dichloroethane (5.2 mL) at room temperature for 30 min. Add sodium triacetoxyborohydride (307 mg, 1.45 mmol) and stir the mixture at room temperature overnight. Concentrate the mixture under reduced pressure, then add 1,4-dioxane (5 mL) and a solution of HCl in 1,4-dioxane (4.0 M, 3.0 mL, 12.0 mmol). Stir the resulting suspension for 10 min, then remove the solids by filtration and concentrate the filtrate under reduced pressure to furnish the title compound (320 mg, 100% yield). Mass spectrum (m/z): 266 (M+H)$^+$, 288 (M+Na)$^+$.

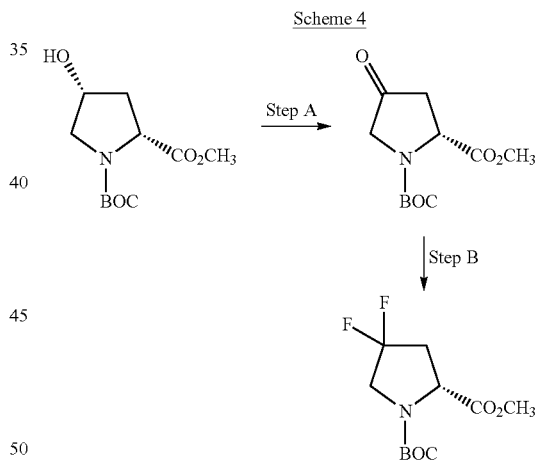

Scheme 4

PREPARATION 15

Synthesis of methyl (R)-1-tert-butoxycarbonyl-4-oxopyrrolidine-2-carboxylate

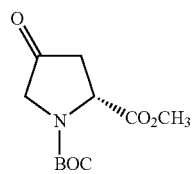 [SMILES: COC(=O)[C@H]1CC(=O)CN1C(=O)OC(C)(C)C]

Scheme 4, Step A: Stir a mixture of N-tert-butyl-cis-4-hydroxy-D-proline methyl ester (2.0 g, 7.91 mmol), the Dess-Martin periodinane (4.84 g, 11.07 mmol), and CH$_2$Cl$_2$ (10 mL) at room temperature for 2 h. Add CH$_2$Cl$_2$ (150 mL), saturated aqueous NaHCO$_3$ (75 mL), and water (75 mL), then separate the layers and extract the aqueous layer with CH$_2$Cl$_2$ (100 mL). Combine the organic phases, dry over MgSO$_4$, filter, and concentrate the filtrate under reduced pressure. Subject the resulting crude material to flash chromatography on silica gel, eluting with a gradient of 0% to 50% EtOAc in hexanes, to furnish the title compound (1.39 g, 72% yield). Mass spectrum (m/z): 144 (M+2H-Boc)$^+$, 188 (M+2H-t-Bu)$^+$.

PREPARATION 16

Synthesis of methyl (R)-1-tert-butoxycarbonyl-4,4-difluoropyrrolidine-2-carboxylate

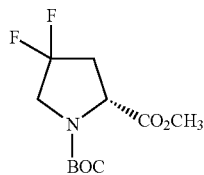

Scheme 4, Step B: Under a nitrogen atmosphere, dissolve methyl (R)-1-tert-butoxycarbonyl-4-oxopyrrolidine-2-carboxylate (270 mg, 1.11 mmol) in CH$_2$Cl$_2$ (2.22 mL) and add bis(2-methoxyethyl)aminosulfur trifluoride (491 mg, 2.22 mmol). Stir the mixture at room temperature overnight, then pour the mixture over a mixture of ice (50 mL) and saturated aqueous NaHCO$_3$ (50 mL). Stir the resulting biphasic mixture for 15 minutes, then extract with EtOAc (50 mL), and concentrate the organic phase under reduced pressure. Subject the resulting crude material to flash chromatography on silica gel, eluting with a gradient of 10% to 50% EtOAc in hexanes, to furnish the title compound (206 mg, 70% yield) as a 53:47 mixture of carbamate rotamers. $^1$H NMR (CDCl$_3$, 400 MHz): δ 4.54 (dd, J=8.8, 6.0 Hz, 0.47 H), 4.44 (dd, J=9.1, 4.9 Hz, 0.53 H), 3.90-3.74 (m, 2H), 3.762 (s, 1.59 H), 3.759 (s, 1.41 H), 2.78-2.61 (m, 1H), 2.52-2.39 (m, 1H), 1.47 (s, 4.23 H), 1.42 (s, 4.77 H).

PREPARATION 17

Synthesis of (±)-2-tert-butoxycarbonyl-1,2,3,4-tetrahydroisoquinoline-1-carboxylic acid (racemic)

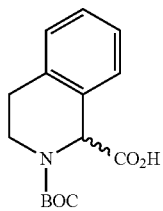 [SMILES: CC(C)(C)OC(=O)N1CCc2ccccc2C1C(=O)O]

To a stirring mixture of (±)-1,2,3,4-tetrahydroisoquinoline-1-carboxylic acid (150 mg, 0.85 mmol) and CH$_2$Cl$_2$ (1.69 mL) at 0° C., add di-tert-butyldicarbonate (185 mg, 0.85 mmol) and triethylamine (177 µL, 1.27 mmol). Allow the mixture to warm to room temperature with stirring overnight. Add an aqueous solution of HCl (1.0 N) until the pH reaches 3.0, then extract the mixture with EtOAc (3×25 mL). Wash the combined organic phases with saturated aqueous NaCl (50 mL), dry over MgSO$_4$, filter, and concentrate the filtrate under reduced pressure to furnish the title compound (235 mg, 100% yield). Mass spectrum (m/z): 222 (M+2H-t-Bu)$^+$, 300 (M+Na)$^+$, 577 (2M+Na)$^+$.

PREPARATION 18

Synthesis of sodium (2R*,6R*)-6-methyl-1-(2-phenoxyethyl)piperidine-2-carboxylate (racemic)

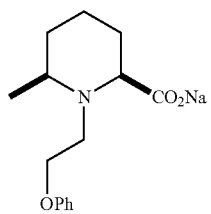

Dissolve ethyl (2R*,6R*)-6-methyl-1-(2-phenoxyethyl)piperidine-2-carboxylate (200 mg, 0.69 mmol) in a mixture of THF (1.0 mL) and CH$_3$OH (1.0 mL), then add an aqueous solution of NaOH (5.0 N, 275 µL, 1.37 mmol) and stir the mixture at room temperature overnight. Concentrate the mixture under reduced pressure to furnish the title compound (196.5 mg, 100% yield). Mass spectrum (m/z): 264 (M+H)$^+$, 549 (2M+Na)$^+$.

PREPARATION 19

Synthesis of (R)-6-tert-butoxycarbonyl-6-azaspiro[2.5]octane-5-carboxylic acid

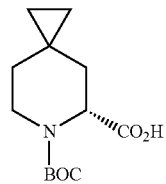

Dissolve methyl (R)-6-tert-butoxycarbonyl-6-azaspiro[2.5]octane-5-carboxylate (1.08 g, 4.01 mmol) in a mixture of THF (20 mL) and CH$_3$OH (10 mL), then add an aqueous solution of NaOH (2.0 N, 10 mL, 20 mmol) and stir the mixture at room temperature for 1.5 h. Add an aqueous solution of HCl (1.0 N) until the pH reaches 1.0, then extract the mixture with EtOAc (3×50 mL). Wash the combined organic layers with a saturated aqueous NaCl solution (50 mL), separate the layers, dry the organic layer over Na$_2$SO$_4$, filter, and concentrate the filtrate under reduced pressure to furnish a mixture containing the title compound (850 mg, 83% yield). Mass spectrum (m/z): 156 (M+2H-Boc)$^+$, 278 (M+Na)$^+$.

Prepare the following compounds essentially by the method of Preparation 19, using the appropriate esters in place of methyl (R)-6-tert-butoxycarbonyl-6-azaspiro[2.5]octane-5-carboxylate:

| No. | Chemical Name | Structure | MS (m/z) | NMR |
|---|---|---|---|---|
| 20 | (1R*,4R,6R*)-3-tert-butoxycarbonyl-3-azabicyclo[4.1.0]heptane-4-carboxylic acid | 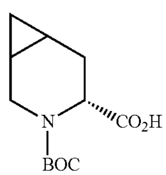 | 142 (M + 2H − Boc)⁺, 186 (M + 2H − t-Bu)⁺, 264 (M + Na)⁺ | |
| 21 | (±)-1-benzyloxycarbonyl-4,4-difluoropiperidine-2-carboxylic acid | 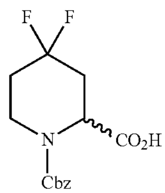 [SMILES: O=C(O)C1CC(F)(F)CCN1C(=O)OCc1ccccc1] | 317 (M + NH₄)⁺, 322 (M + Na)⁺ | |
| 22 | (±)-1-tert-butoxycarbonyl-5,5-difluoropiperidine-2-carboxylic acid | 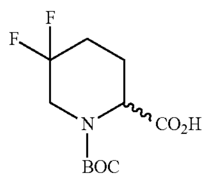 | 288 (M + Na)⁺ | |
| 23 | (2R,4S)-1-tert-butoxycarbonyl-4-hydroxypiperidine-2-carboxylic acid | 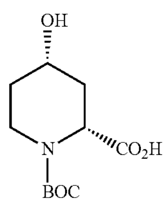 [SMILES: CC(C)(C)OC(=O)N1CC[C@H](O)C[C@@H]1C(=O)O] | | (CDCl₃, 400 MHz) δ 4.87-4.78 (m, 0.6H), 4.71-4.64 (m, 0.4H), 4.20-4.15 (m, 1H), 3.94-3.85 (m, 0.4H), 3.85-3.73 (m, 0.6H), 3.45-3.27 (m, 1H), 2.46-2.42 (m, 0.4H), 2.42-2.37 (m, 0.6H), 1.94 (dd, J = 6.9, 2.4 Hz, 0.6H), 1.90 (dd, J = 6.8, 2.4 Hz, 0.4H), 1.77-1.61 (m, 4H), 1.47 (s, 9H) |
| 24 | (R)-1-tert-butoxycarbonyl-4,4-difluoropyrrolidine-2-carboxylic acid | 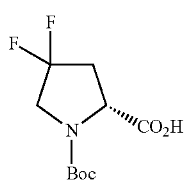 | | (CD₃OD, 400 MHz) δ 4.48 (dd, J = 9.2, 4.8 Hz, 0.35H), 4.44 (dd, J = 9.2, 4.8 Hz, 0.65H), 3.83-3.68 (m, 2H), 2.90-2.74 (m, 1H), 2.53-2.41 (m, 1H), 1.46 (s, 3.15H), 1.42 (s, 5.85H) |

PREPARATION 25

Synthesis of (±)-1-tert-butoxycarbonyl-4,4-dimethylpiperidine-2-carboxylic acid

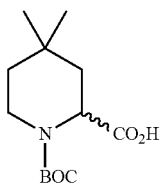 [SMILES: CC1(C)CCN(C(=O)OC(C)(C)C)C(C(=O)O)C1]

In a Parr shaker, pressurize a mixture of benzyl (R)-6-tert-butoxycarbonyl-6-azaspiro[2.5]octane-5-carboxylate (600 mg, 1.74 mmol), glacial acetic acid (10 mL), and 5% palladium on carbon (100 mg, 0.047 mmol) to 413.7 kPag with hydrogen. Shake at room temperature for one hour, then release the pressure and remove the solids by filtration, rinsing through with acetic acid (10 mL). Place the filtrate in a pressure vessel and add platinum(IV) oxide (225 mg, 0.99 mmol). Pressurize the vessel to 1724 kPag with hydrogen, and stir at 100° C. overnight. Cool the vessel to room temperature and release the pressure. Remove the solids by filtration, rinsing through with acetic acid. Concentrate the filtrate under reduced pressure. Add toluene (10 mL), and again concentrate under reduced pressure to furnish a crude, colorless film (329 mg).

To this crude material, add an aqueous solution of sodium hydroxide (2.0 N, 6.3 mL, 12.5 mmol). Then, add a solution of di-tert-butyldicarbonate (300 mg, 1.7 mmol) in 1,4-dioxane (3.4 mL) and stir the mixture at room temperature overnight. Add di-tert-butyldicarbonate (152 mg, 0.70 mmol) and stir at room temperature for 6 h. Neutralize the mixture to pH 7 with 1.0 N aqueous HCl, then add EtOAc (15 mL). Acidify the aqueous layer to pH 3 with 1.0 N HCl, then extract the aqueous layer with EtOAc (3×15 mL) and CH₂Cl₂ (3×15 mL). Further acidify the aqueous layer to pH 2 with 1.0 N aqueous HCl, then extract with EtOAc (5×15 mL). Combine the organic layers, dry over Na₂SO₄, remove the solids by filtration, and concentrate under reduced pressure to furnish the title compound as a colorless film (85.5 mg, 22% yield). Mass spectrum (m/z): 158 (M+H)⁺.

PREPARATION 26

Synthesis of methyl 4-((1S)-1-(((2R*)-1-tert-butoxycarbonyl-2-methylpiperidin-2-carbonyl)amino)ethyl)benzoate

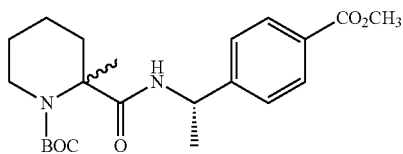 [SMILES: COC(=O)c1ccc([C@H](C)NC(=O)C2(C)CCCCN2C(=O)OC(C)(C)C)cc1]

Add (±)-1-tert-butoxycarbonyl-2-methylpiperidine-2-carboxylic acid (200 mg, 0.82 mmol) and methyl 4-((S)-1-aminoethyl)benzoate hydrochloride (177 mg, 0.82 mmol) to DMF (1.6 mL), then add triethylamine (401 μL 2.9 mmol), followed by BOP (472 mg, 1.07 mmol). Stir the mixture at room temperature overnight. Dilute the mixture with EtOAc (25 mL) and wash with saturated aqueous NaCl (2×25 mL). Dry the organic layer over MgSO₄, filter to remove the solids, and concentrate the filtrate under reduced pressure. Subject the crude material to flash chromatography on silica gel, eluting with a gradient of 20% to 100% EtOAc in hexanes, to furnish the title compound as a colorless oil (158 mg, 48% yield). Mass spectrum (m/z): 305 (M+2H-Boc)⁺.

Prepare the following compounds essentially by the method of Preparation 26, using the appropriate carboxylic acids in place of 1-tert-butoxycarbonyl-2-methylpiperidine-2-carboxylic acid:

| No. | Chemical Name | Structure | MS (m/z) |
|---|---|---|---|
| 27 | methyl 4-((1S)-1-((2R*,6R*)-(1-(2-phenoxyethyl)-6-methylpiperidin-2-carbonyl)amino)ethyl)benzoate | 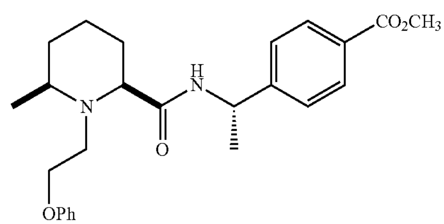 [SMILES: COC(=O)c1ccc([C@H](C)NC(=O)[C@@H]2CCC[C@H](C)N2CCOc2ccccc2)cc1] | 425 (M + H)⁺ |
| 28 | methyl 4-((1S)-1-(((2R*)-1-benzyloxycarbonyl-4,4-difluoropiperidin-2-carbonyl)amino)ethyl)benzoate | 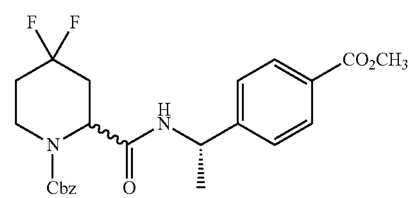 [SMILES: COC(=O)c1ccc([C@H](C)NC(=O)C2CC(F)(F)CCN2C(=O)OCc2ccccc2)cc1] | 461 (M + H)⁺, 483 (M + Na)⁺ |
| 29 | methyl 4-((1S)-1-(((2R*)-1-tert-butoxycarbonyl-5,5-difluoropiperidin-2-carbonyl)amino)ethyl)benzoate | 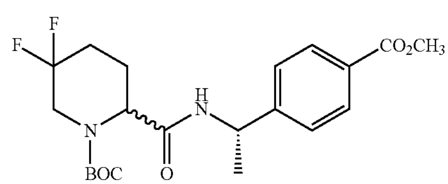 [SMILES: COC(=O)c1ccc([C@H](C)NC(=O)C2CCC(F)(F)CN2C(=O)OC(C)(C)C)cc1] | 327 (M + 2H − Boc)⁺, 449 (M + Na)⁺ |
| 30 | methyl 4-((1S)-1-((2R*,5S*)-(1-(2-phenoxyethyl)-5-hydroxypiperidin-2-carbonyl)amino)ethyl)benzoate | 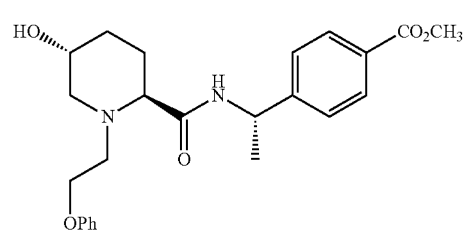 [SMILES: COC(=O)c1ccc([C@H](C)NC(=O)[C@@H]2CC[C@@H](O)CN2CCOc2ccccc2)cc1] | 427 (M + H)⁺, 465 (M + K)⁺ |
| 31 | methyl 4-((1S)-1-(((2R)-1-tert-butoxycarbonylpyrrolidin-2-carbonyl)amino)ethyl)benzoate | Absolute | 277 (M + 2H − Boc)⁺, 321 (M + 2H − t-Bu)⁺, 377 (M + H)⁺, 399 (M + Na)⁺ |

| No. | Chemical Name | Structure | MS (m/z) |
|---|---|---|---|
| 32 | methyl 4-((1S)-1-(((2R)-1-tert-butoxycarbonyl-4,4-difluoropyrrolidin-2-carbonyl)amino)ethyl)benzoate | Absolute | 313 (M + 2H − Boc)+, 357 (M + 2H − t-Bu)+, 435 (M + Na)+, 451 (M + K)+ |
| 33 | methyl 4-((1S)-1-(((1R*)-2-tert-butoxycarbonyl-1,2,3,4-tetrahydroisoquinolin-1-carbonyl)amino)ethyl)benzoate | 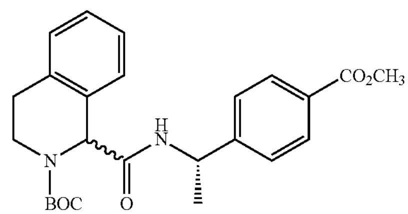 [SMILES: COC(=O)c1ccc([C@H](C)NC(=O)C2c3ccccc3CCN2C(=O)OC(C)(C)C)cc1] | 339 (M + 2H − Boc)+, 383 (M + 2H − t-Bu)+, 439 (M + H)+, 461 (M + Na)+ |

PREPARATION 34

Synthesis of methyl 4-(((1S,3R,4R)-2-tert-butoxycarbonyl-2-azabicyclo[2.2.1]heptan-3-carbonyl)aminomethyl)benzoate

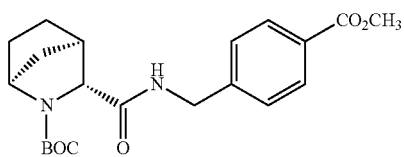 [SMILES: COC(=O)c1ccc(CNC(=O)[C@H]2[C@@H]3CC[C@@H](C3)N2C(=O)OC(C)(C)C)cc1]

Stir a mixture of (1S,3R,4R)-2-tert-butoxycarbonyl-2-azabicyclo[2.2.1]heptane-3-carboxylic acid (253 mg, 1.05 mmol), methyl 4-(aminomethyl)benzoate hydrochloride (260 mg, 1.29 mmol), 1-hydroxybenzotriazole hydrate (60 mg, 0.39 mmol), triethylamine (600 μL 4.30 mmol), EDC (300 mg, 1.56 mmol), and CH$_2$Cl$_2$ (20 mL) at room temperature for two days. Wash the mixture with an aqueous solution of hydrochloric acid (1.0 N, 25 mL), followed by a saturated aqueous solution of NaHCO$_3$ (50 mL) and a saturated aqueous solution of NaCl (50 mL). Dry the organic phase over MgSO$_4$, filter, and concentrate under reduced pressure to furnish a glassy oil containing approximately 85% of the title compound by mass (450 mg, 94% yield). Mass spectrum (m/z): 289 (M+2H−Boc)+, 333 (M+2H-t-Bu)+, 411 (M+Na)+.

Prepare the following compounds essentially by the method of Preparation 34, using the appropriate carboxylic acids in place of (1S,3R,4R)-2-tert-butoxycarbonyl-2-azabicyclo[2.2.1]heptane-3-carboxylic acid, and using methyl 4-((S)-1-aminoethyl)benzoate or methyl 4-((S)-1-aminoethyl)benzoate hydrochloride in place of methyl 4-(aminomethyl)benzoate hydrochloride:

| No. | Chemical Name | Structure | MS (m/z) | Note |
|---|---|---|---|---|
| 35 | methyl 4-((1S)-1-(((1S,3R,4R)-2-tert-butoxycarbonyl-2-azabicyclo[2.2.1]heptan-3-carbonyl)amino)ethyl)benzoate | 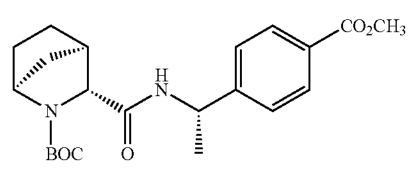 [SMILES: COC(=O)c1ccc([C@H](C)NC(=O)[C@H]2[C@@H]3CC[C@@H](C3)N2C(=O)OC(C)(C)C)cc1] | 303 (M + 2H − Boc)+, 347 (M + 2H − t-Bu)+, 403 (M + H)+, 425 (M + Na)+ | |
| 36 | methyl 4-((1S)-1-(((5R)-6-tert-butoxycarbonyl-6-azaspiro[2.5]octane-5-carbonyl)amino)ethyl)benzoate | 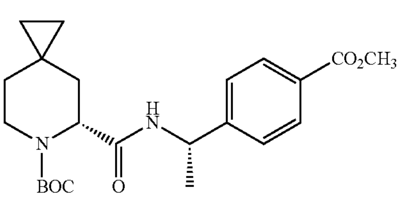 [SMILES: COC(=O)c1ccc([C@H](C)NC(=O)[C@H]2CC3(CCN2C(=O)OC(C)(C)C)CC3)cc1] | 317 (M + 2H − Boc)+, 361 (M + 2H − t-Bu)+, 439 (M + Na)+ | a |

-continued

| No. | Chemical Name | Structure | MS (m/z) | Note |
|---|---|---|---|---|
| 37 | methyl 4-((1S)-1-(((1R*, 4R,6R*)-3-tert-butoxycarbonyl-3-azabicyclo[4.1.0]heptane-4-carbonyl)amino)ethyl)benzoate | 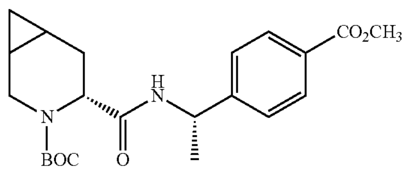 [SMILES: COC(=O)c1ccc([C@H](C)NC(=O)[C@H]2CC3CC3CN2C(=O)OC(C)(C)C)cc1] | 303 (M + 2H − Boc)+, 347 (M + 2H − t-Bu)+, 403 (M + H)+, 425 (M + Na)+ | b |
| 38 | methyl 4-((1S)-1-(((2R*)-1-tert-butoxycarbonyl-4,4-dimethylpiperidin-2-carbonyl)amino)ethyl)benzoate | 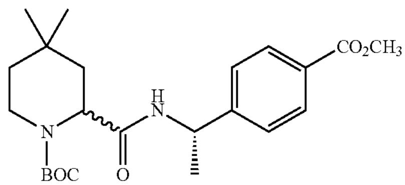 [SMILES: COC(=O)c1ccc([C@H](C)NC(=O)C2CC(C)(C)CCN2C(=O)OC(C)(C)C)cc1] | 319 (M + 2H − Boc)+, 441 (M + Na)+ | b |
| 39 | methyl 4-((1S)-1-(((2R)-1-tert-butoxycarbonyl-4-oxopiperidin-2-carbonyl)amino)ethyl)benzoate | 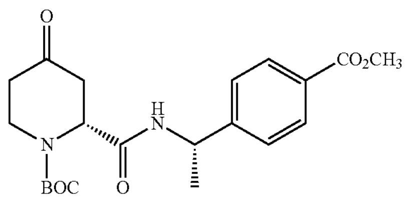 [SMILES: COC(=O)c1ccc([C@H](C)NC(=O)[C@H]2CC(=O)CCN2C(=O)OC(C)(C)C)cc1] | 305 (M + 2H − Boc)+, 349 (M + 2H − t-Bu)+, 427 (M + Na)+ | b |
| 40 | methyl 4-((1S)-1-(((2R,4S)-1-tert-butoxycarbonyl-4-hydroxypiperidin-2-carbonyl)amino)ethyl)benzoate | | 307 (M + 2H − Boc)+, 351 (M + 2H − t-Bu)+, 407 (M + H)+, 429 (M + Na)+ | b | a) Purify the product by reverse-phase chromatography on C18 silica gel, eluting with 0.1% formic acid in a water/acetonitrile gradient.
b) Purify the product by flash chromatography on silica gel, eluting with an EtOAc/hexanes gradient.

PREPARATION 41

Synthesis of methyl 4-((1S)-1-(((2R,4S)-1-tert-butoxycarbonyl-4-methoxypiperidin-2-carbonyl)amino)ethyl)benzoate

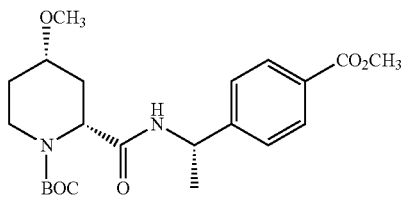 [SMILES: COC(=O)c1ccc([C@H](C)NC(=O)[C@H]2C[C@@H](OC)CCN2C(=O)OC(C)(C)C)cc1]

Cool a mixture of methyl 4-((1S)-1-(((2R,4S)-1-tert-butoxycarbonyl-4-hydroxypiperidin-2-carbonyl)amino)ethyl)benzoate (440 mg, 1.08 mmol), THF (5.0 mL), and iodomethane (67 µL, 1.08 mmol) to 0° C., then add sodium hydride (60% dispersion in mineral oil, 43.3 mg, 1.08 mmol) and stir for 2 h at 0° C. Add a second portion of sodium hydride (60% dispersion in mineral oil, 43.3 mg, 1.08 mmol), stir at 0° C. for 3 h, then allow to warm temperature with stirring overnight. Add a saturated aqueous solution of NH$_4$Cl (5 mL), then extract the mixture with EtOAc (10 mL). Wash the combined organic layers with a saturated aqueous solution of NaCl (10 mL), then dry over Na$_2$SO$_4$, remove the solids by filtration, and concentrate the filtrate under reduced pressure. Subject the crude material to flash chromatography on silica gel, eluting with a gradient of 0% to 40% EtOAc in hexanes, to furnish the title compound as a clear, colorless oil (128 mg, 28% yield). Mass spectrum (m/z): 365 (M+2H-t-Bu)+, 421 (M+H)+.

PREPARATION 42

Synthesis of methyl 4-((1S)-1-(((2R*)-2-methylpiperidin-2-carbonyl)amino)ethyl)benzoate hydrochloride

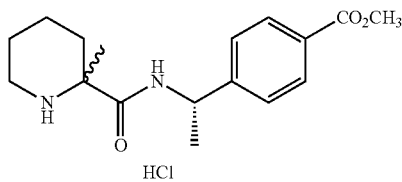 [SMILES: COC(=O)c1ccc([C@H](C)NC(=O)C2(C)CCCCN2)cc1 ; Cl]

Treat methyl 4-((1S)-1-(((2R*)-1-tert-butoxycarbonyl-2-methylpiperidin-2-carbonyl)amino)ethyl)benzoate (158 mg, 0.39 mmol) with a 4.0 M solution of hydrogen chloride in dioxane (2.0 mL, 8.0 mmol) and stir for one hour at room temperature. Concentrate the mixture under reduced pressure to furnish the title compound as a white solid (133 mg, 100% yield). Mass spectrum (m/z): 305 (M+H)$^+$.

Prepare the following compounds essentially by the method of Preparation 42, using the appropriate tert-butyl carbamates in place of methyl 4-((1S)-1-(((2R*)-1-tert-butoxycarbonyl-2-methylpiperidin-2-carbonyl)amino)ethyl)benzoate:

| No. | Chemical Name | Structure | MS (m/z) | Note |
|---|---|---|---|---|
| 43 | methyl 4-(((1S,3R,4R)-2-azabicyclo[2.2.1]heptan-3-carbonyl)aminomethyl)benzoate hydrochloride | 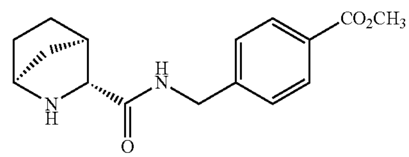 | 289 (M + H)$^+$, 599 (2M + Na)$^+$ | a, b |
| 44 | methyl 4-((1S)-1-(((1S,3R,4R)-2-azabicyclo[2.2.1]heptan-3-carbonyl)amino)ethyl)benzoate hydrochloride | 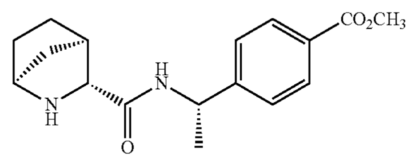 | 303 (M + H)$^+$, 605 (2M + H)$^+$, 627 (2M + Na)$^+$ | a, c |
| 45 | methyl 4-((1S)-1-(((2R*)-5,5-difluoropiperidin-2-carbonyl)amino)ethyl)benzoate hydrochloride | 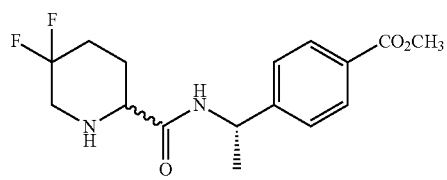 | 327 (M + H)$^+$, 653 (2M + H)$^+$, 675 (2M + Na)$^+$ | |
| 46 | methyl 4-((1S)-1-(((2R)-pyrrolidin-2-carbonyl)amino)ethyl)benzoate hydrochloride | 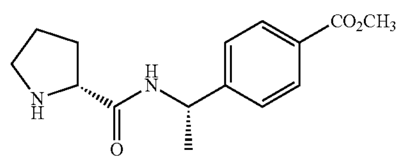 | 277 (M + H)$^+$, 553 (2M + H)$^+$, 575 (2M + Na)$^+$ | d |
| 47 | methyl 4-((1S)-1-(((2R)-4,4-difluoropyrrolidin-2-carbonyl)amino)ethyl)benzoate hydrochloride | 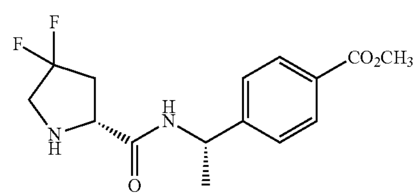 | 313 (M + H)$^+$, 625 (2M + H)$^+$, 647 (2M + Na)$^+$ | d |
| 48 | methyl 4-((1S)-1-(((1R*)-1,2,3,4-tetrahydroisoquinolin-1-carbonyl)amino)ethyl)benzoate hydrochloride | | 339 (M + H)$^+$, 677 (2M + H)$^+$, 699 (2M + Na)$^+$ | | a) Use CH$_3$OH (20 mL/mmol substrate) as a co-solvent.
b) Stir for three days at room temperature instead of one hour.
c) Stir for three hours at room temperature, then add a second portion of HCl in 1,4-dioxane (equal to the first), and stir for two more hours at room temperature, instead of simply stirring for one hour at room temperature.
d) Use CH$_2$Cl$_2$ (1 mL/mmol substrate) as a co-solvent.

PREPARATION 49

Synthesis of methyl 4-((1S)-1-(((5R)-6-azaspiro[2.5]octane-5-carbonyl)amino)ethyl)benzoate

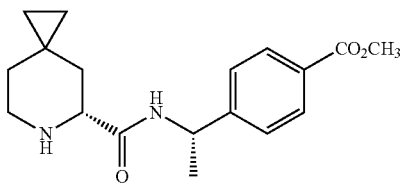 [SMILES: COC(=O)c1ccc([C@H](C)NC(=O)[C@H]2CC3(CCN2)CC3)cc1]

Dissolve methyl 4-((1S)-1-(((5R)-6-tert-butoxycarbonyl-6-azaspiro[2.5]octane-5-carbonyl)amino)ethyl)benzoate (60 mg, 0.14 mmol) in $CH_2Cl_2$ (2.0 mL) and add trifluoroacetic acid (1.0 mL, 13.23 mmol). Stir the mixture at room temperature for 90 minutes, then add water (7.0 mL) and a 10% aqueous solution of sodium carbonate (20 mL). Extract the mixture with EtOAc (3×50 mL), and wash the combined organic layers with a saturated aqueous solution of NaCl (5 mL). Dry the organic phase over $Na_2SO_4$, filter, and concentrate the filtrate under reduced pressure to furnish a mixture containing ca. 84% of the title compound by mass (53 mg, 97% corrected yield). Mass spectrum (m/z): 317 $(M+H)^+$, 633 $(2M+H)^+$, 655 $(2M+Na)^+$.

Prepare the following compounds essentially by the method of Preparation 49, using the appropriate tert-butyl carbamates in place of methyl 4-((1S)-1-(((5R)-6-tert-butoxycarbonyl-6-azaspiro[2.5]octane-5-carbonyl)amino)ethyl)benzoate:

| No. | Chemical Name | Structure | MS (m/z) |
|---|---|---|---|
| 50 | methyl 4-((1S)-1-(((1R*,4R,6R*)-3-azabicyclo[4.1.0]heptane-4-carbonyl)amino)ethyl)benzoate (2:1 mixture of distereomers) | 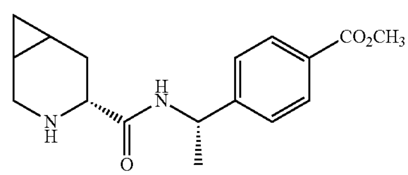 [SMILES: COC(=O)c1ccc([C@H](C)NC(=O)[C@H]2CC3CC3CN2)cc1] | 303 $(M + H)^+$, 605 $(2M + H)^+$, 627 $(2M + Na)^+$ |
| 51 | methyl 4-((1S)-1-(((2R*)-4,4-dimethylpiperidin-2-carbonyl)amino)ethyl)benzoate | 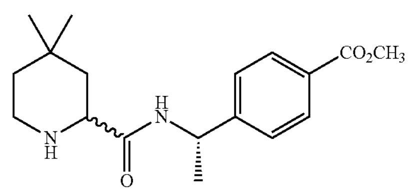 [SMILES: COC(=O)c1ccc([C@H](C)NC(=O)C2CC(C)(C)CCN2)cc1] | 319 $(M + H)^+$, 637 $(2M + H)^+$ |
| 52 | methyl 4-((1S)-1-(((2R)-4-oxopiperidin-2-carbonyl)amino)ethyl)benzoate | 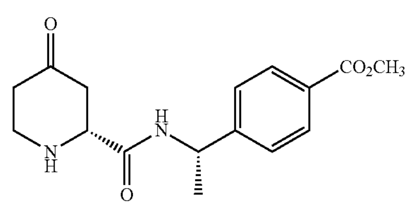 [SMILES: COC(=O)c1ccc([C@H](C)NC(=O)[C@H]2CC(=O)CCN2)cc1] | 305 $(M + H)^+$ |
| 53 | methyl 4-((1S)-1-(((2R,4S)-4-hydroxypiperidin-2-carbonyl)amino)ethyl)benzoate | 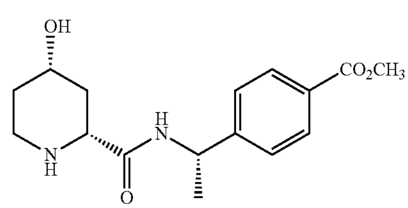 [SMILES: COC(=O)c1ccc([C@H](C)NC(=O)[C@H]2C[C@@H](O)CCN2)cc1] | 307 $(M + H)^+$, 613 $(2M + H)^+$, 635 $(2M + Na)^+$ |
| 54 | methyl 4-((1S)-1-(((2R,4S)-4-methoxypiperidin-2-carbonyl)amino)ethyl)benzoate | 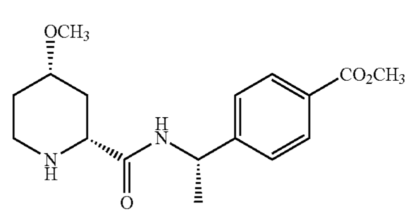 [SMILES: COC(=O)c1ccc([C@H](C)NC(=O)[C@H]2C[C@@H](OC)CCN2)cc1] | 321 $(M + H)^+$, 343 $(M + Na)^+$, 641 $(2M + H)^+$, 663 $(2M + Na)^+$ |

PREPARATION 55

Synthesis of methyl 4-((1S)-1-(((2R*)-4,4-difluoropiperidin-2-carbonyl)amino)ethyl)benzoate

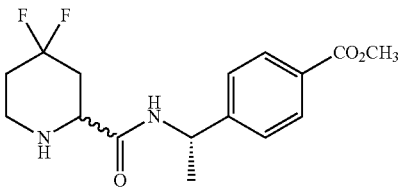 [SMILES: COC(=O)c1ccc([C@H](C)NC(=O)C2CC(F)(F)CCN2)cc1]

Dissolve methyl 4-((1S)-1-(((2R*)-1-benzyloxycarbonyl-4,4-difluoropiperidin-2-carbonyl)amino)ethyl)benzoate (540 mg, 1.17 mmol) in CH$_3$OH (4.7 mL) and add 10% palladium on carbon (125 mg, 0.12 mmol). Stir at room temperature under a hydrogen atmosphere for three days. Filter through a plug of diatomaceous earth, rinsing through with CH$_3$OH (10 mL). Concentrate the filtrate under reduced pressure to furnish the title compound as a white solid (280 mg, 73% yield). Mass spectrum (m/z): 327 (M+H)$^+$, 653 (2M+H)$^+$, 675 (2M+Na)$^+$.

PREPARATION 56

Synthesis of methyl 4-((1S)-1-(((2R*)-1-(2-phenoxyethyl)-2-methylpiperidin-2-carbonyl)amino)ethyl)benzoate

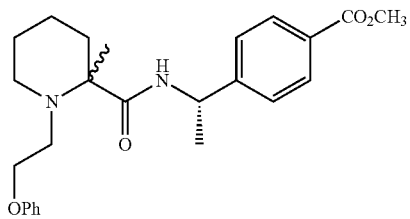 [SMILES: COC(=O)c1ccc([C@H](C)NC(=O)C2(C)CCCCN2CCOc2ccccc2)cc1]

Stir a mixture of methyl 4-((1S)-1-((2R*)-2-methylpiperidin-2-carbonyl)amino)ethyl)benzoate hydrochloride (130 mg, 0.38 mmol) and 2-phenoxyacetaldehyde (104 mg, 0.76 mmol) in 1,2-dichloroethane (1.9 mL) at room temperature for 30 minutes, then add sodium triacetoxyborohydride (113 mg, 0.53 mmol) and stir at room temperature for 3 h. Cool the mixture to 0° C. and add a saturated aqueous solution of NaHCO$_3$ (25 mL). Extract the mixture with EtOAc (2×25 mL), and wash the combined organic layers with a saturated aqueous solution of NaCl (25 mL). Separate the organic layer and dry over MgSO$_4$, filter, and concentrate the filtrate under reduced pressure. Subject the crude material to flash chromatography on silica gel, eluting with a gradient of 0% to 100% EtOAc in hexanes, to furnish 130 mg of material. Subject this material to reverse-phase chromatography on C18 silica gel, eluting with 0.1% formic acid in a water/CH$_3$CN gradient. Extract the fractions containing the title compound with EtOAc (2×50 mL)), and wash the combined organic layers with a saturated aqueous solution of NaCl (25 mL). Separate the organic layer and dry over MgSO$_4$, filter, and concentrate the filtrate under reduced pressure to furnish the title compound as a colorless oil (75 mg, 46% yield). Mass spectrum (m/z): 425 (M+H)$^+$.

Prepare the following compounds essentially by the method of Preparation 56, using the appropriate amine hydrochloride salts in place of methyl 4-((1S)-1-(((2R*)-2-methylpiperidin-2-carbonyl)amino)ethyl)benzoate hydrochloride and/or the appropriate aldehydes in place of 2-phenoxyacetaldehyde:

| No. | Chemical Name | Structure | MS (m/z) | Note |
|---|---|---|---|---|
| 57 | methyl 4-((1S)-1-(((2R)-1-(2-(4-fluorophenoxy)ethyl)-5,5-difluoropiperidin-2-carbonyl)amino)ethyl)benzoate | 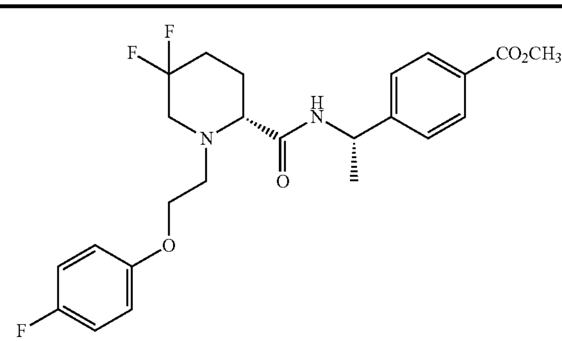 | 465 (M + H)$^+$, 487 (M + Na)$^+$ | a |
| 58 | methyl 4-((1S)-1-(((1R*)-2-(2-phenoxyethyl)-1,2,3,4-tetrahydroisoquinolin-1-carbonyl)amino)ethyl)benzoate | | 459 (M + H)$^+$, 481 (M + Na)$^+$ | b | a) Purify by flash chromatography on silica gel, eluting with a gradient of 10% to 90% EtOAc in hexanes. The title compound is the second diastereomer to elute. No reverse-phase chromatography.
b) Purify by flash chromatography on silica gel, eluting with a gradient of 0% to 80% EtOAc in hexanes. No reverse-phase chromatography.

PREPARATION 59

Synthesis of methyl 4-(((1S,3R,4R)-2-(2-phenoxyethyl)-2-azabicyclo[2.2.1]heptan-3-carbonyl)aminomethyl)benzoate

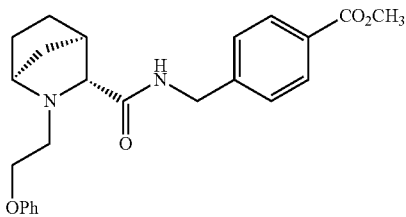 [SMILES: COC(=O)c1ccc(CNC(=O)[C@H]2[C@@H]3CC[C@@H](C3)N2CCOc2ccccc2)cc1]

Dissolve methyl 4-(((1S,3R,4R)-2-azabicyclo[2.2.1]heptan-3-carbonyl)aminomethyl)benzoate hydrochloride (300 mg, 0.92 mmol) and 2-phenoxyacetaldehyde (140 mg, 1.03 mmol) in CH$_3$OH (5 mL) at room temperature, and add acetic acid (200 µL, 3.49 mmol) and sodium cyanoborohydride (300 mg, 4.77 mmol). Stir the mixture at room temperature overnight. Concentrate the mixture under reduced pressure, and add EtOAc (20 mL) and saturated aqueous NaHCO$_3$ (20 mL). Separate the layers, and wash the organic layer with a saturated aqueous solution of NaCl (20 mL). Concentrate the organic layer under reduced pressure, then subject the crude material to flash chromatography on silica gel, eluting with a gradient of 100% EtOAc to 5% (7.0 M NH$_3$ in CH$_3$OH) in EtOAc, to furnish the title compound as a glassy oil (240 mg, 64% yield). Mass spectrum (m/z): 409 (M+H)$^+$, 431 (M+Na)$^+$.

Prepare the following compounds essentially by the method of Preparation 59, using the appropriate amine hydrochloride salts in place of methyl 4-(((1S,3R,4R)-2-azabicyclo[2.2.1]heptan-3-carbonyl)aminomethyl)benzoate hydrochloride:

| No. | Chemical Name | Structure | MS (m/z) | Note |
|---|---|---|---|---|
| 60 | methyl 4-((1S)-1-(((1S,3R,4R)-2-(2-phenoxyethyl)-2-azabicyclo[2.2.1]heptan-3-carbonyl)amino)ethyl)benzoate | 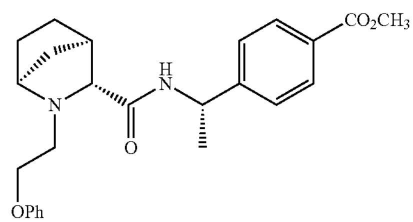 [SMILES: COC(=O)c1ccc([C@H](C)NC(=O)[C@H]2[C@@H]3CC[C@@H](C3)N2CCOc2ccccc2)cc1] | 423 (M + H)$^+$ | |
| 61 | methyl 4-((1S)-1-(((2R)-1-(2-phenoxyethyl)-4,4-difluoropiperidin-2-carbonyl)amino)ethyl)benzoate | 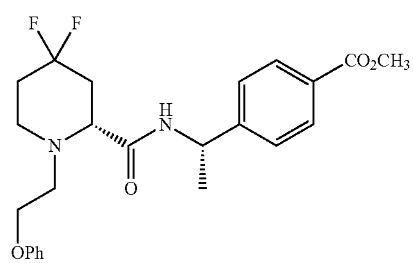 [SMILES: COC(=O)c1ccc([C@H](C)NC(=O)[C@H]2CC(F)(F)CCN2CCOc2ccccc2)cc1] | 447 (M + H)$^+$, 469 (M + Na)$^+$ | a, b |
| 62 | methyl 4-((1S)-1-(((2S)-1-(2-phenoxyethyl)-4,4-difluoropiperidin-2-carbonyl)amino)ethyl)benzoate | | 447 (M + H)$^+$, 469 (M + Na)$^+$ | a, b | a) No normal-phase flash chromatography.

b) Preparations 61 and 62 emanate from the same distereomerically impure starting material. Separate the diastereomers by reverse-phase chromatography on C18 silica gel, eluting with 0.1% formic acid in a CH$_3$CN/water gradient.

PREPARATION 63

Synthesis of methyl 4-((1S)-1-(((5R)-6-(2-(4-fluorophenoxy)ethyl)-6-azaspiro[2.5]octane-5-carbonyl)amino)ethyl)benzoate

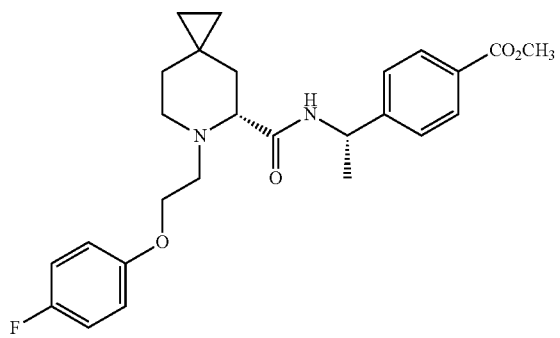 [SMILES: COC(=O)c1ccc([C@H](C)NC(=O)[C@H]2CC3(CCN2CCOc2ccc(F)cc2)CC3)cc1]

Dissolve methyl 4-((1S)-1-(((5R)-6-azaspiro[2.5]octane-5-carbonyl)amino)ethyl)benzoate (44 mg, 0.14 mmol) in DMF (1.5 mL) at room temperature, then add DIEA (73 µL, 0.42 mmol), 1-(2-bromoethoxy)-4-fluorobenzene (46 mg, 0.21 mmol), and NaI (10.5 mg, 0.07 mmol). Heat the mixture to 110° C. for 2 h with stirring. Dilute the mixture with TBME (25 mL) and wash with a 5% aqueous solution of LiCl (25 mL), followed by a saturated aqueous solution of NaCl (25 mL). Dry the organic layer over $Na_2SO_4$, filter, and concentrate under reduced pressure. Subject the crude material to flash chromatography on silica gel, eluting with a gradient of 0% to 100% EtOAc in hexanes, to furnish the title compound as a white solid (38 mg, 60% yield). Mass spectrum (m/z): 455 $(M+H)^+$.

Prepare the following compounds essentially by the method of Preparation 63, using the appropriate amines in place of methyl 4-((1S)-1-(((5R)-6-azaspiro[2.5]octane-5-carbonyl)amino)ethyl)benzoate and/or the appropriate alkyl bromides in place of 1-(2-bromoethoxy)-4-fluorobenzene:

| No. | Chemical Name | Structure | MS (m/z) | Note |
|-----|---------------|-----------|----------|------|
| 64 | methyl 4-((1S)-1-(((5R)-6-(2-phenoxyethyl)-6-azaspiro[2.5]octane-5-carbonyl)amino)ethyl)benzoate | 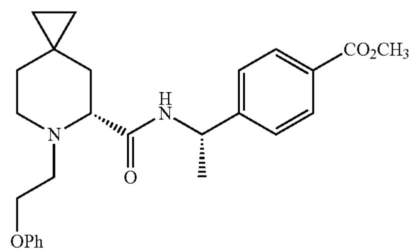 [SMILES: COC(=O)c1ccc([C@H](C)NC(=O)[C@H]2CC3(CCN2CCOc2ccccc2)CC3)cc1] | 437 $(M+H)^+$ | |
| 65 | methyl 4-((1S)-1-((((1S,4R,6S)-3-(2-phenoxyethyl)-3-azabicyclo[4.1.0]heptane-4-carbonyl)amino)ethyl)benzoate | 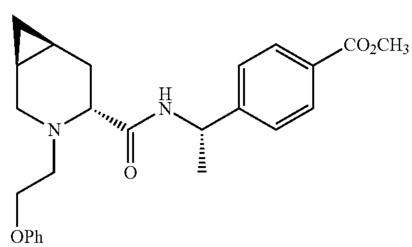 [SMILES: COC(=O)c1ccc([C@H](C)NC(=O)[C@H]2C[C@@H]3C[C@@H]3CN2CCOc2ccccc2)cc1] | 423 $(M+H)^+$ | a |
| 66 | methyl 4-((1S)-1-(((2R)-1-(2-phenoxyethyl)-4,4-dimethylpiperidin-2-carbonyl)amino)ethyl)benzoate | 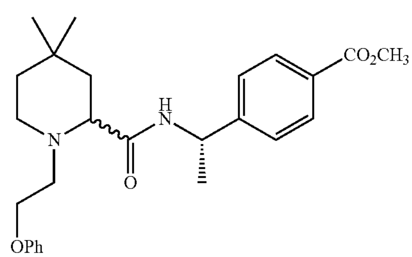 [SMILES: COC(=O)c1ccc([C@H](C)NC(=O)C2CC(C)(C)CCN2CCOc2ccccc2)cc1] | 439 $(M+H)^+$ | |
| 67 | methyl 4-((1S)-1-(((2R)-1-(2-phenoxyethyl)-4-oxopiperidin-2-carbonyl)amino)ethyl)benzoate | 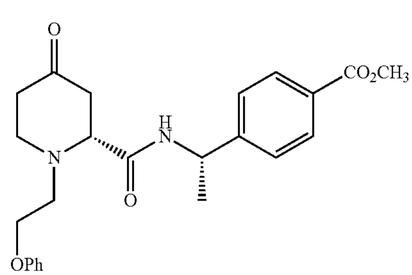 [SMILES: COC(=O)c1ccc([C@H](C)NC(=O)[C@H]2CC(=O)CCN2CCOc2ccccc2)cc1] | 425 $(M+H)^+$, 447 $(M+Na)^+$ | |

| No. | Chemical Name | Structure | MS (m/z) | Note |
|---|---|---|---|---|
| 68 | methyl 4-((1S)-1-(((2R,4S)-1-(2-phenoxyethyl)-4-hydroxypiperidin-2-carbonyl)amino)ethyl)benzoate | 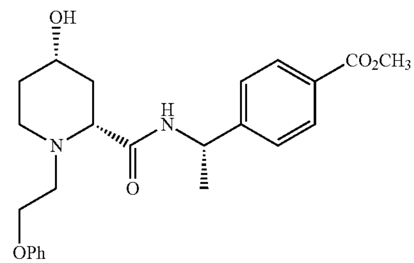 [SMILES: COC(=O)c1ccc([C@H](C)NC(=O)[C@H]2C[C@@H](O)CCN2CCOc2ccccc2)cc1] | 427 (M + H)+, 449 (M + Na)+ | |
| 69 | methyl 4-((1S)-1-(((2R,4S)-1-(2-phenoxyethyl)-4-methoxypiperidin-2-carbonyl)amino)ethyl)benzoate | | 441 (M + H)+ | | a) Purify by flash column chromatography on silica gel, eluting with a 0% to 70% EtOAc/hexanes gradient to obtain a mixture of diastereomers. Then, purify by flash column chromatography on silica gel, eluting with 52% EtOAc in hexanes, to separate the diastereomers. The title compound is the first diastereomer to elute.

PREPARATION 70

Synthesis of methyl 4-((1S)-1-(((2R)-1-(2-(4-fluorophenoxy)ethyl)pyrrolidin-2-carbonyl)amino)ethyl)benzoate

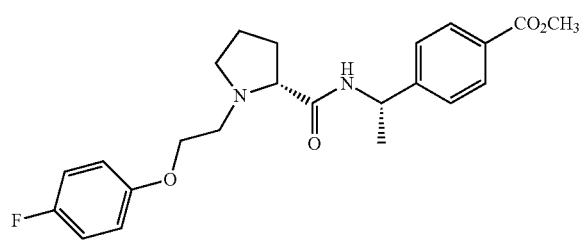 [SMILES: COC(=O)c1ccc([C@H](C)NC(=O)[C@H]2CCCN2CCOc2ccc(F)cc2)cc1]

Dissolve methyl 4-((1S)-1-(((2R)-pyrrolidin-2-carbonyl)amino)ethyl)benzoate hydrochloride (1.00 g, 3.2 mmol) in DMF (8.0 mL) at room temperature, then add $K_2CO_3$ (1.33 g, 9.6 mmol) and 1-(2-bromoethoxy)-4-fluorobenzene (715 mg, 3.2 mmol), then heat the mixture to 100° C. with stirring overnight. Dilute the mixture with EtOAc (100 mL), and wash with a saturated aqueous solution of NaCl (2×75 mL). Discard the aqueous layers, and dry the organic layer over $MgSO_4$, filter, and concentrate under reduced pressure to a volume of ca. 10 mL. Add hexanes (100 mL, then collect the resulting precipitate by filtration and rinse with hexanes (25 mL) and air-dry to furnish the title compound as a white solid (750 mg, 57% yield). Mass spectrum (m/z): 415 (M+H)+.

Prepare the following compound essentially by the method of Preparation 70, using methyl 4-((1S)-1-(((2R)-4,4-difluoropyrrolidin-2-carbonyl)amino)ethyl)benzoate hydrochloride in place of methyl 4-((1S)-1-(((2R)-pyrrolidin-2-carbonyl)amino)ethyl)benzoate hydrochloride:

| No. | Chemical Name | Structure | MS (m/z) | Note |
|---|---|---|---|---|
| 71 | methyl 4-((1S)-1-(((2R)-1-(2-(4-fluorophenoxy)ethyl)4,4-difluoropyrrolidin-2-carbonyl)amino)ethyl)benzoate | | 451 (M + H)+, 473 (M + Na)+ | a, b | a) after heating overnight, add one equivalent of NaI and one additional equivalent of alkyl bromide.
b) Purify by flash column chromatography on silica gel, eluting with a 10% to 100% EtOAc/hexanes gradient.

EXAMPLE 1

Synthesis of 4-((1S)-1-(((2R*)-1-(2-phenoxyethyl)-2-methylpiperidin-2-carbonyl)amino)ethyl)benzoic acid hydrochloride

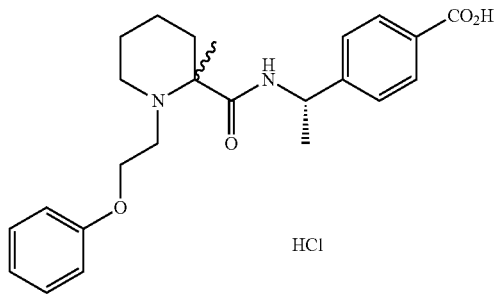 [SMILES: C[C@H](NC(=O)C1(C)CCCCN1CCOc1ccccc1)c1ccc(C(=O)O)cc1 ; Cl]

HCl

Dissolve methyl 4-((1S)-1-(((2R*)-1-(2-phenoxyethyl)-2-methylpiperidin-2-carbonyl)amino)ethyl)benzoate (70 mg, 0.16 mmol) in a mixture of THF (1.0 mL) and $CH_3OH$ (1.0 mL). Add a 1.0 N aqueous solution of sodium hydroxide (330 μL, 0.33 mmol), and stir the mixture at room temperature overnight. Concentrate the mixture under reduced pressure to furnish a solid, then add a 4.0 M solution of hydrogen chloride in 1,4-dioxane (2.0 mL, 8.0 mmol) and stir at room temperature for 10 min. Remove the solids by filtration, rinsing through with THF (2 mL). Concentrate the filtrate under reduced pressure to furnish the title compound as an off-white solid (52 mg, 71% yield). Mass spectrum (m/z): 411 $(M+H)^+$.

Prepare the following compounds essentially by the method of Example 1, using the appropriate methyl esters in place of methyl 4-((1S)-1-(((2R*)-1-(2-phenoxyethyl)-2-methylpiperidin-2-carbonyl)amino)ethyl)benzoate:

| Ex. | Chemical Name | Structure | MS (m/z) | Note |
|---|---|---|---|---|
| 2 | 4-((1S)-1-((2R*,6R*)-(1-(2-phenoxyethyl)-6-methylpiperidin-2-carbonyl)amino)ethyl)benzoic acid hydrochloride | 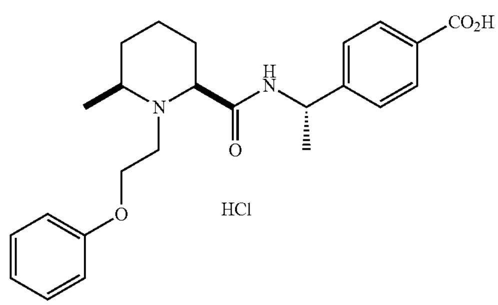 [SMILES: C[C@H](NC(=O)[C@@H]1CCC[C@H](C)N1CCOc1ccccc1)c1ccc(C(=O)O)cc1 ; Cl] | 411 $(M + H)^+$ | |
| 3 | 4-(((1S,3R,4R)-2-(2-phenoxyethyl)-2-azabicyclo[2.2.1]heptan-3-carbonyl)aminomethyl)benzoic acid | 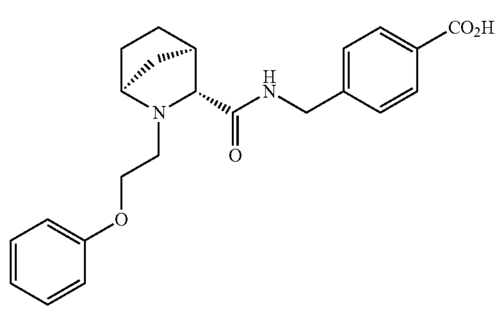 [SMILES: O=C(O)c1ccc(CNC(=O)[C@H]2[C@@H]3CC[C@@H](C3)N2CCOc2ccccc2)cc1] | 395 $(M + H)^+$ | a, b |
| 4 | 4-((1S)-1-(((1S,3R,4R)-2-(2-phenoxyethyl)-2-azabicyclo[2.2.1]heptan-3-carbonyl)amino)ethyl)benzoic acid | 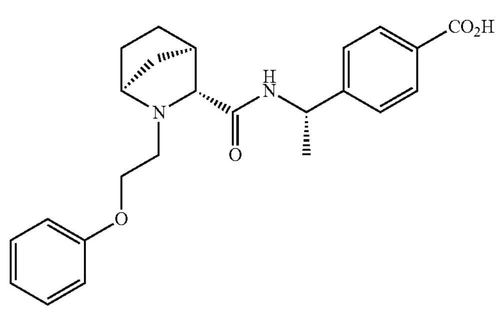 [SMILES: C[C@H](NC(=O)[C@H]1[C@@H]2CC[C@@H](C2)N1CCOc1ccccc1)c1ccc(C(=O)O)cc1] | 409 $(M + H)^+$ | a, b, c |

| Ex. | Chemical Name | Structure | MS (m/z) | Note |
|---|---|---|---|---|
| 5 | 4-((1S)-1-(((5R)-6-(2-(4-fluorophenoxy)ethyl)-6-azaspiro[2.5]octane-5-carbonyl)amino)ethyl)benzoic acid | 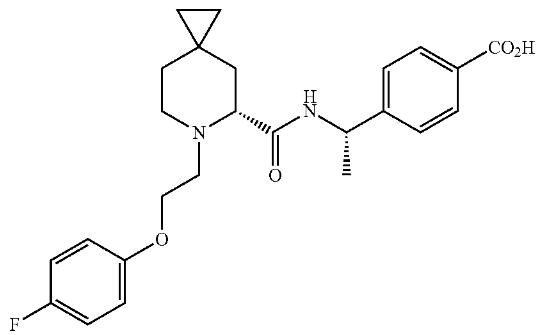 [SMILES: C[C@H](NC(=O)[C@H]1CC2(CCN1CCOc1ccc(F)cc1)CC2)c1ccc(C(=O)O)cc1] | 441 (M + H)+ | d |
| 6 | 4-((1S)-1-(((5R)-6-(2-phenoxyethyl)-6-azaspiro[2.5]octane-5-carbonyl)amino)ethyl)benzoic acid | 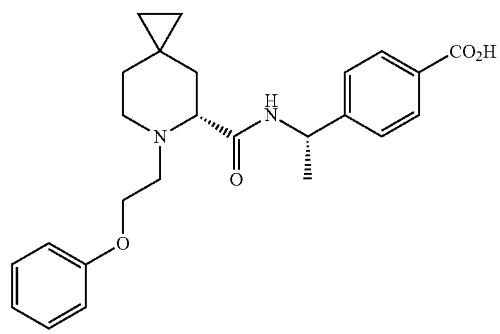 [SMILES: C[C@H](NC(=O)[C@H]1CC2(CCN1CCOc1ccccc1)CC2)c1ccc(C(=O)O)cc1] | 423 (M + H)+ | d |
| 7 | 4-((1S)-1-(((1S,4R,6S)-3-(2-phenoxyethyl)-3-azabicyclo[4.1.0]heptane-4-carbonyl)amino)ethyl)benzoic acid | 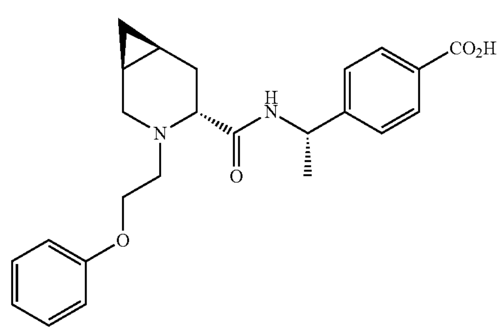 [SMILES: C[C@H](NC(=O)[C@H]1C[C@@H]2C[C@@H]2CN1CCOc1ccccc1)c1ccc(C(=O)O)cc1] | 409 (M + H)+ | e |
| 8 | 4-((1S)-1-(((2R)-1-(2-phenoxyethyl)-4,4-difluoropiperidin-2-carbonyl)amino)ethyl)benzoic acid hydrochloride | 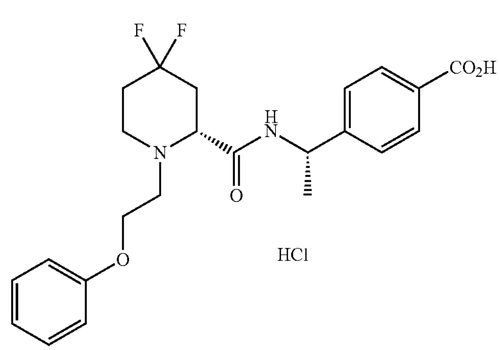 [SMILES: C[C@H](NC(=O)[C@H]1CC(F)(F)CCN1CCOc1ccccc1)c1ccc(C(=O)O)cc1 ; Cl] | 433 (M + H)+ | |

-continued

| Ex. | Chemical Name | Structure | MS (m/z) | Note |
|---|---|---|---|---|
| 9 | 4-((1S)-1-(((2S)-1-(2-phenoxyethyl)-4,4-difluoropiperidin-2-carbonyl)amino)ethyl)benzoic acid hydrochloride | 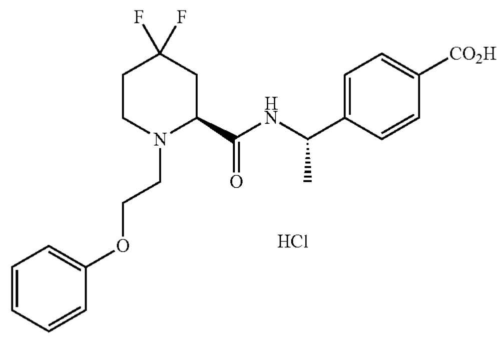 [SMILES: C[C@H](NC(=O)[C@@H]1CC(F)(F)CCN1CCOc1ccccc1)c1ccc(C(=O)O)cc1 ; Cl] | 433 (M + H)+, 455 (M + Na)+ | |
| 10 | 4-((1S)-1-(((2R)-1-(2-(4-fluorophenoxy)ethyl)-5,5-difluoropiperidin-2-carbonyl)amino)ethyl)benzoic acid trifluoroacetate | 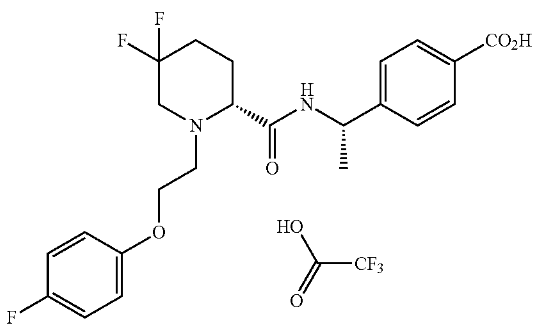 [SMILES: C[C@H](NC(=O)[C@H]1CCC(F)(F)CN1CCOc1ccc(F)cc1)c1ccc(C(=O)O)cc1 ; O=C(O)C(F)(F)F] | 451 (M + H)+ | f, g |
| 11 | 4-((1S)-1-(((2R*)-1-(2-phenoxyethyl)-4,4-dimethylpiperidin-2-carbonyl)amino)ethyl)benzoic acid | 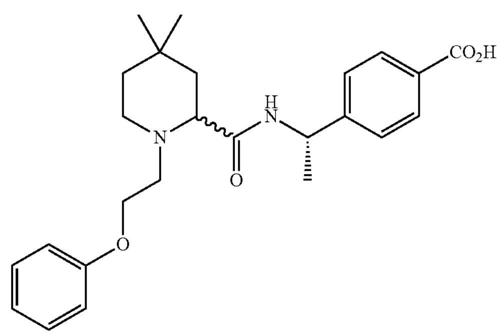 [SMILES: C[C@H](NC(=O)C1CC(C)(C)CCN1CCOc1ccccc1)c1ccc(C(=O)O)cc1] | 425 (M + H)+ | c |
| 12 | 4-((1S)-1-(((2R)-1-(2-phenoxyethyl)-4-oxopiperidin-2-carbonyl)amino)ethyl)benzoic acid trifluoroacetate | 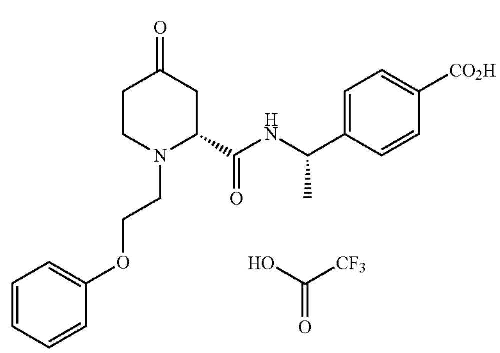 [SMILES: C[C@H](NC(=O)[C@H]1CC(=O)CCN1CCOc1ccccc1)c1ccc(C(=O)O)cc1 ; O=C(O)C(F)(F)F] | 411 (M + H)+ | d, g |

-continued

| Ex. | Chemical Name | Structure | MS (m/z) | Note |
|---|---|---|---|---|
| 13 | 4-((1S)-1-(((2R,4S)-1-(2-phenoxyethyl)-4-hydroxypiperidin-2-carbonyl)amino)ethyl)benzoic acid | 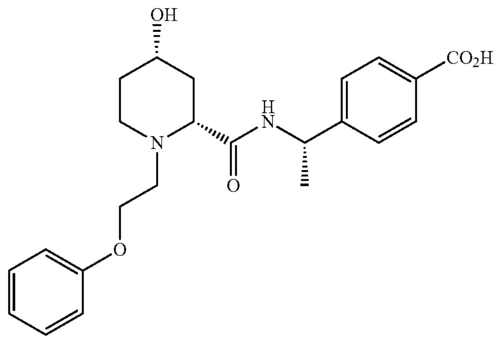 [SMILES: C[C@H](NC(=O)[C@H]1C[C@@H](O)CCN1CCOc1ccccc1)c1ccc(C(=O)O)cc1] | 413 (M + H)+ | d |
| 14 | 4-((1S)-1-(((2R,4S)-1-(2-phenoxyethyl)-4-methoxypiperidin-2-carbonyl)amino)ethyl)benzoic acid | 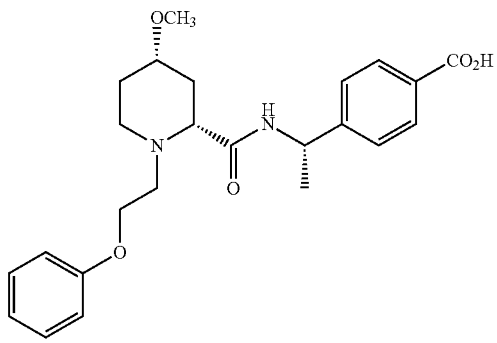 [SMILES: CO[C@H]1CCN(CCOc2ccccc2)[C@@H](C(=O)N[C@@H](C)c2ccc(C(=O)O)cc2)C1] | 427 (M + H)+ | d |
| 15 | 4-((1S)-1-(((2R*,5S*)-1-(2-phenoxyethyl)-5-hydroxypiperidin-2-carbonyl)amino)ethyl)benzoic acid hydrochloride | 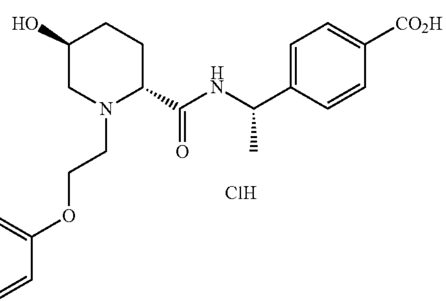 | 413 (M + H)+, 435 (M + Na)+ | d |
| 16 | 4-((1S)-1-(((2R)-1-2-(4-fluorophenoxy)ethyl)pyrrolidin-2-carbonyl)amino)ethyl)benzoic acid hydrochloride | 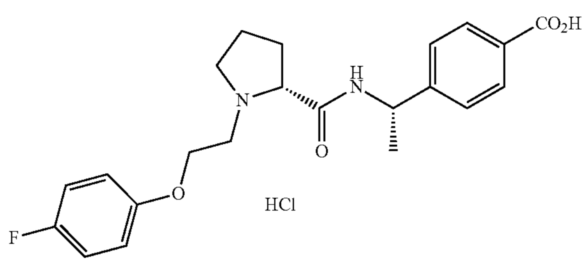 [SMILES: C[C@H](NC(=O)[C@H]1CCCN1CCOc1ccc(F)cc1)c1ccc(C(=O)O)cc1 ; Cl] | 401 (M + H)+ | h |
| 17 | 4-((1S)-1-(((2R)-1-(2-(4-fluorophenoxy)ethyl)-4,4-difluoropyrrolidin-2-carbonyl)amino)ethyl)benzoic acid | 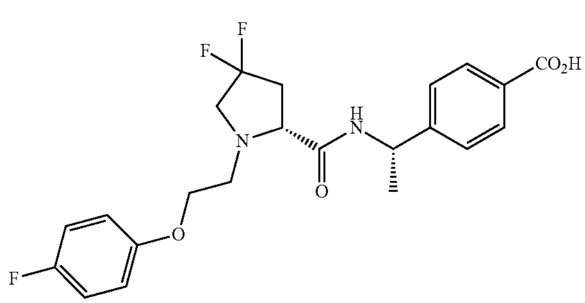 [SMILES: C[C@H](NC(=O)[C@H]1CC(F)(F)CN1CCOc1ccc(F)cc1)c1ccc(C(=O)O)cc1] | 437 (M + H)+ | i |

| Ex. | Chemical Name | Structure | MS (m/z) | Note |
|---|---|---|---|---|
| 18 | 4-((1S)-1-(((1R)-2-(2-phenoxyethyl)-1,2,3,4-tetrahydroisoquinolin-1-carbonyl)amino)ethyl)benzoic acid hydrochloride | | 445 (M + H)+ | g | a) Instead of acidifying with HCl/1,4-dioxane, neutralize the reaction mixture with 5.0 N aqueous HCl, concentrate under reduced pressure, triturate the material with EtOAc, and decant the solution phase, then remove the solvent to obtain the product.
b) Stir the reaction mixture at 70° C. for two hours rather than at room temperature overnight.
c) Purify by flash column chromatography on silica gel, eluting with a 0% to 10% CH$_3$OH/EtOAc gradient.
d) Instead of acidifying with HCl/1,4-dioxane, neutralize the reaction mixture to pH 7.0 with 1.0 N aqueous HCl, then extract with EtOAc, wash with saturated aqueous NaCl, dry the organic phase over Na$_2$SO$_4$, filter, and concentrate under reduced pressure to obtain the product.
e) Instead of acidifying with HCl/1,4-dioxane, neutralize the reaction mixtureto pH 7.0 with 1.0 N aqueous HCl, then concentrate under reduced pressure, triturate the material with 1:1 ethanol/CH$_3$CN, sonicate, and remove the solids by filtration through a PTFE filter disc. Concentrate the filtrate under reduced pressure to obtain the product.
f) Instead of acidifying with HCl/1,4-dioxane, concentrate the reaction mixture under reduced pressure.
g) Subject the crude material to reverse-phase chromatography on C18 silica gel, eluting with 0.1% TFA in a CH$_3$CN/water gradient to obtain the product as a single diastereomer.
h) Instead of acidifying with HCl/1,4-dioxane, concentrate under reduced pressure to remove the organic solvents, acidify the reaction mixture to pH 1.0 with 5.0 N aqueous HCl, and isolate the resulting white precipitate by filtration to obtain the product.
i) Instead of acidifying with HCl/1,4-dioxane, concentrate under reduced pressure to remove the organic solvents, acidify the reaction mixture to pH 4.0 with 5.0 N aqueous HCl, and isolate the resulting white precipitate by filtration to obtain the product.

EXAMPLE 19

Synthesis of 4-((1S)-1-(((2R)-1-(2-phenoxyethyl)-5,5-difluoropiperidin-2-carbonyl)amino)ethyl)benzoic acid hydrochloride

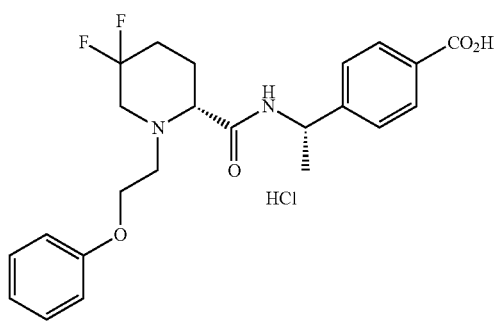 [SMILES: C[C@H](NC(=O)[C@H]1CCC(F)(F)CN1CCOc1ccccc1)c1ccc(C(=O)O)cc1 ; Cl]

Stir a mixture of methyl 4-((1S)-1-(((2R*)-5,5-difluoropiperidin-2-carbonyl)amino)ethyl)benzoate hydrochloride (200 mg, 0.55 mmol), β-bromophenetole (113 mg, 0.55 mmol), potassium carbonate (229 mg, 1.65 mmol), CH$_3$CN (1.38 mL), and water (at least 9.9 mg, 0.55 mmol but not more than 29.7 mg, 1.65 mmol) at 70° C. for two days, then at 82° C. for three days. Concentrate the mixture under reduced pressure to furnish a solid. Stir this solid in boiling ethanol, filter, and concentrate the filtrate under reduced pressure. Subject the crude material to reverse-phase chromatography on C18 silica gel, eluting with 0.1% formic acid in a CH$_3$CN/water gradient, to furnish 161 mg of a mixture of diastereomers of the title compound. Subject 125 mg of this mixture to preparatory supercritical fluid chromatography on a Chiralcel OJ-H 5 μM column, eluting with 0.2% isopropylamine in a 3:1 mixture of supercritical CO$_2$ to CH$_3$OH. Isolate the second isomer to elute, and concentrate under reduced pressure. Treat the material with a 4.0 M solution of HCl in 1,4-dioxane (5 mL) and stir for 10 minutes. Concentrate under reduced pressure to furnish the title compound as a white solid (54 mg, 27% yield). Mass spectrum (m/z): 433 (M+H)+, 455 (M+Na)+.

In Vitro Binding to Human EP1, EP2, EP3 and EP4 hEP1 and hEP4 membranes are prepared from recombinant HEK293 cells stably expressing human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

Kd values for [3H]-PGE$_2$ binding to each receptor are determined by saturation binding studies or homologous competition. Compounds are tested in a 96-well format using a three-fold dilution series to generate a 10-point curve. Diluted compound is incubated with 20 μg/well EP1, 10 μg/well EP2, 1 ug/well EP3 or 10 to 20 μg/well EP4 membrane for 90 minutes at 25° C. in the presence of 0.3 to 0.5 nM [$^3$H]-PGE$_2$ (PerkinElmer, 118 to 180 Ci/mmol). The binding reaction is performed in 200 µL MES buffer (10 mM MES pH 6.0 with KOH, 10 mM MgCl$_2$ and 1 mM EDTA) using 0.5 mL polystyrene 96-well deep-well plates. Non-specific binding is calculated by comparing binding in the presence and absence of 2 µM of PGE$_2$. The membranes are harvested by filtration (TomTek harvester), washed 4 times with cold buffer (10 mM MES pH 6.0 with KOH, 10 mM MgCl$_2$), dried in a 60° C. oven, and the radioactivity is quantified as counts per minute (CPM) using a TopCount detector. Percent specific binding is calculated as the percent of the binding in the absence of any inhibitor, corrected for binding in the presence of 2 uM of PGE$_2$. Data are analyzed using a 4-parameter nonlinear logistic equation (ABase Equation 205) as shown: y=(A+((B−A)/(1+((C/x)^D)))) where, y=% specific inhibition, A=bottom of the curve; B=top of the curve; C=relative IC$_{50}$=concentration causing 50% inhibition based on the range of the data from top to bottom; D=Hill, Slope=slope of the curve. K$_i$ conversion from IC$_{50}$ Values (K$_i$=IC$_{50}$/(1+[L]/K$_d$) where [L] is the ligand concentration). Results are expressed as the geometric mean±standard deviation; n=number of independent determinations. The standard deviation is calculated by the delta method, being SD$_{log\ Ki}$×geometric mean×ln(10).

The compounds of Examples 1-19 herein are tested essentially as described above and exhibit a K$_i$ value for hEP4 of lower than about 2 µM.

TABLE 1

In vitro binding of Example 8 to human EP1, EP2, EP3 and EP4

| Test Compound | hEP1, K$_i$ (nM) | hEP2, K$_i$ (nM) | hEP3, K$_i$ (nM) | hEP4, K$_i$ (nM) |
|---|---|---|---|---|
| Example 8 | >12500 (n = 1) | 956 (n = 1) | >14800 (n = 1) | 3.68 ± 3.32 (n = 6) |

The data in table 1 demonstrate the compound of Example 8 binds to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 geneticin and 2 mM L-glutamine. Confluent cultures are grown at 37° C. in an atmosphere containing 5% CO$_2$. Cells are harvested using 2.5% Trypsin-EDTA, suspended in freeze media (FBS with 6% DMSO) at 10$^7$ cells/mL and aliquots are stored in liquid nitrogen. Just before assay, cells are thawed in DMEM, centrifuged, and resuspended in cAMP buffer.

The inhibition of PGE$_2$-stimulated cAMP production by EP4 antagonists is measured using HTRF; (Cisbio catalog #62AM4PEB). An aliquot equivalent to 4000 cells is incubated with 50 µL cAMP assay buffer containing EC$_{80}$ of PGE$_2$ (0.188 nM PGE$_2$ from Sigma, catalog # P5640-10 mg) and antagonists at room temperature for 20 minutes. cAMP assay buffer contains 500 mL HBSS (Hank's Balanced Salt Solution), 0.1% BSA, 20 mM HEPES and 200 µM IBMX (Sigma 15879). CJ-042794 (4-{(1S)-1-[({5-chloro-2-[(4-fluorophenyl)oxy]phenyl}carbonyl)amino]ethyl}benzoic acid) serves as a positive control (See Murase, A., et al., *Life Sciences*, 82:226-232 (2008)). To measure the cAMP levels, cAMP-d2 conjugate and anti cAMP-cryptate conjugate in lysis buffer are incubated with the treated cells at room temperature for 1 hour. The HTRF signal is detected using an EnVision® plate reader (Perkin-Elmer) to calculate the ratio of fluorescence at 665 nm to 620 nm. The raw data are converted to cAMP amount (pmole/well) using a cAMP standard curve generated for each experiment. Data are analyzed using a 4-parameter nonlinear logistic equation (ABase Equation 205) as shown: y=(A+((B−A)/(1+((C/x)^D)))) where, y=% specific inhibition, A=Bottom of the curve, B=Top of the curve, C=Relative IC$_{50}$=concentration causing 50% inhibition based on the range of the data from top to bottom, D=Hill, Slope=slope of the curve. Results are expressed as the geometric mean±standard deviation; n=number of independent determinations. The standard deviation is calculated by the delta method, being SD$_{log\ Ki}$×geometric mean×ln(10).

Following the procedures essentially as described above, the compound of Example 8 has an IC$_{50}$ of 1.76±1.51 nM (n=6) measured at human EP4. This demonstrates that the compound of Example 8 is an antagonist of human EP4 in vitro.

In Vitro Antagonist Activity in Human Whole Blood

The inhibitory effects of PGE$_2$ on LPS-induced TNFα production from macrophages/monocytes are believed to be mediated by EP4 receptors (See Murase, A., et al., *Life Sciences*, 82:226-232 (2008)). The ability of the compound of Example 8 to reverse the inhibitory effect of PGE$_2$ on LPS-induced TNFα production in human whole blood is an indicia of functional activity.

Blood is collected from normal volunteer donors into sodium heparin vacutainer tubes. Donors have not taken NSAIDs or celecoxib within 48 hours or glucocorticoids within two weeks of the donation. All tubes/donor are pooled into 50 mL Falcon conical centrifuge tubes and 98 µL/well is distributed into 96-well tissue culture plates (Falcon 3072). Compounds are diluted into DMSO to 100× final and 1 µL/well in triplicate is added to the blood to give 7 point concentration response curves. The blood is pretreated with the compounds at 37° C., in a 5% CO$_2$ humidified atmosphere, for 30 minutes, after which 1 µL/well of a solution of 1 mg/mL of lipopolysaccharide (LPS) (Sigma 0111:B4) in 0.2 mg/mL bovine serum albumin (BSA)/PBS+/−1 mM PGE$_2$ (Cayman 14010) is added to give a final LPS concentration of 10 µg/mL+/−10 nM PGE$_2$. The plates are incubated for 20-24 hours at 37° C. in a 5% CO$_2$ humidified atmosphere. The plates are centrifuged at 1800× g, 10 minutes at 22° C., in an Eppendorf 5810R centrifuge. Plasma is removed from the cell layer and is transferred to v-bottom polypropylene plates. TNFα levels in 2 µL plasma are quantified by a commercially available enzyme immunoassay (R&D Systems DY210), using Immulon 4 HBX plates (Thermo 3855) and 3,3',5,5' tetramethylbiphenyl-4,4'-diamine substrate (KPL 50-76-03). The plates are read at A$_{450}$-A$_{650}$ on a plate reader (Molecular Devices Versamax) using SOFTmaxPRO (v. 4.3.1) software. IC$_{50}$s are calculated using Graphpad Prism (v. 4) nonlinear regression, sigmoidal dose response curve fitting. Results are expressed as the geometric mean±standard deviation; n=number of independent determinations The standard deviation is calculated by the delta method, being SD$_{log\ Ki}$×geometric mean×ln(10).

Following the procedures essentially as described above, the compound of Example 8 has an IC$_{50}$ of 0.0782±0.061 uM (n=6) measured at human EP4. This demonstrates that the compound of Example 8 is an EP4 antagonist in the human blood TNFα induction assay.

We claim:
1. A compound of the formula:

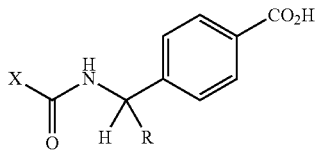

wherein X is:

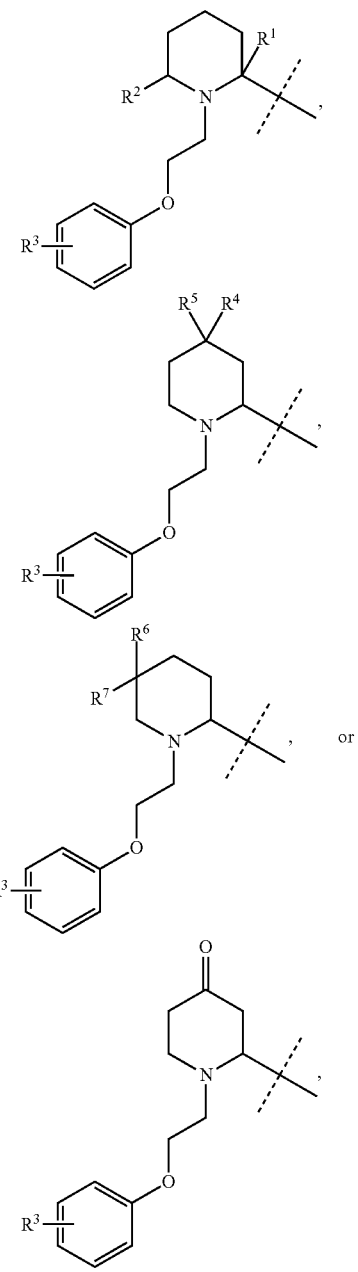

R is H, methyl, or ethyl;
R$^1$ is methyl, when R$^2$ is H, and R$^1$ is H when R$^2$ is methyl;
R$^3$ is H or F;
R$^4$ is H, F, or methyl;
R$^5$ is OH, methyl, methoxy, or F; and
R$^6$ is H when R$^7$ is OH, and R$^6$ is F when R$^7$ is F;
or a pharmaceutically acceptable salt thereof.

2. The compound or salt according to claim 1 wherein R is methyl.

3. The compound or salt according to claim 2 wherein R$^4$ is F and R$^5$ is F.

4. The compound or salt according to claim 2 wherein R$^4$ is methyl and R$^5$ is methyl.

5. The compound or salt according to claim 1 wherein X is:

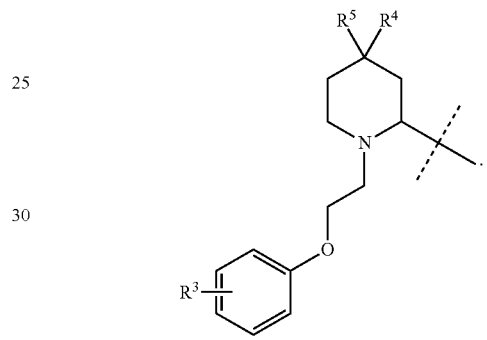

6. The compound or salt according to claim 1 wherein X is:

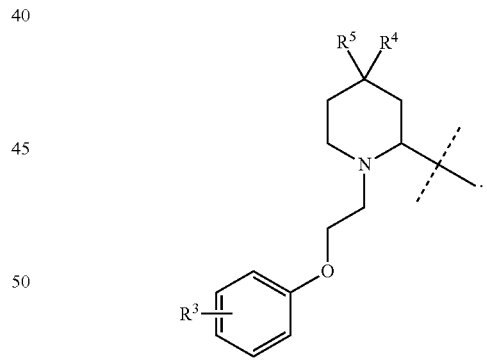

7. A pharmaceutical composition, comprising a compound or a pharmaceutically acceptable salt thereof according to claim 1 with one or more pharmaceutically acceptable carriers, diluents, or excipients.

* * * * *